United States Patent [19]

Zheng et al.

[11] Patent Number: 5,698,542

[45] Date of Patent: Dec. 16, 1997

[54] BONE RESORPTION INHIBITION/ OSTEOGENESIS PROMOTION PHARMACEUTICAL COMPOSITION

[75] Inventors: Hu Zheng; Lingling Weng, both of Chengdu, China

[73] Assignees: Iskra Industry Co., Ltd., Tokyo, Japan; Institute of Pharmacology, West China Univ. of Medical Sciences, Chengdu, China

[21] Appl. No.: 507,382

[22] PCT Filed: Dec. 28, 1994

[86] PCT No.: PCT/JP94/02303

§ 371 Date: Aug. 29, 1995

§ 102(e) Date: Aug. 29, 1995

[87] PCT Pub. No.: WO95/18141

PCT Pub. Date: Jul. 6, 1995

[30] Foreign Application Priority Data

Dec. 29, 1993 [JP] Japan ..................... 5-355404

[51] Int. Cl.$^6$ ................................. A61K 31/65
[52] U.S. Cl. ................................. 514/152
[58] Field of Search ........................... 514/152

[56] References Cited

U.S. PATENT DOCUMENTS 4,925,833  5/1990  McNamara et al. ............. 514/152

FOREIGN PATENT DOCUMENTS

| | | |
|---|---|---|
| 29 32 606 | 2/1980 | Germany . |
| 39 07 290 | 9/1990 | Germany . |
| 62-26256 | 2/1987 | Japan . |
| 2-36145 | 2/1990 | Japan . |
| 4-352795 | 12/1992 | Japan . |
| 2201419 | 9/1988 | United Kingdom . |
| 94/21667 | 9/1994 | WIPO . |

OTHER PUBLICATIONS

M.W. Orme et al., "Synthesis of β–Estradiol–3–Benzoate–17–(Succinyl–12A–Tetracycline): A Potential Bone–Seeking Estrogen", Bioorganic & Medicinal Chemistry Letters, vol. 4, No. 11, Jun. 1994, pp. 1375–1380.

*Primary Examiner*—Theodore J. Criares
*Attorney, Agent, or Firm*—Foley & Lardner

[57] ABSTRACT

A pharmaceutical composition comprising a compound represented by the following formula (I):

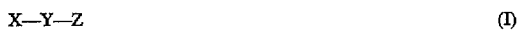

[where Y is represented by the following formula (III):

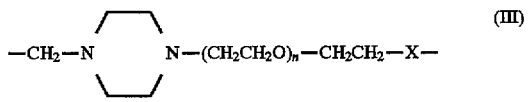

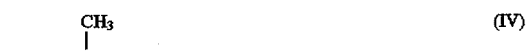

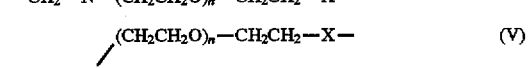

X is a monovalent group of a tetracycline type compound, and Z is a monovalent group of asteroid type compound such as estrogen].

The compound can concentrate on the bone tissue and has a bone resorption inhibition/ossification promotion functions.

10 Claims, 7 Drawing Sheets

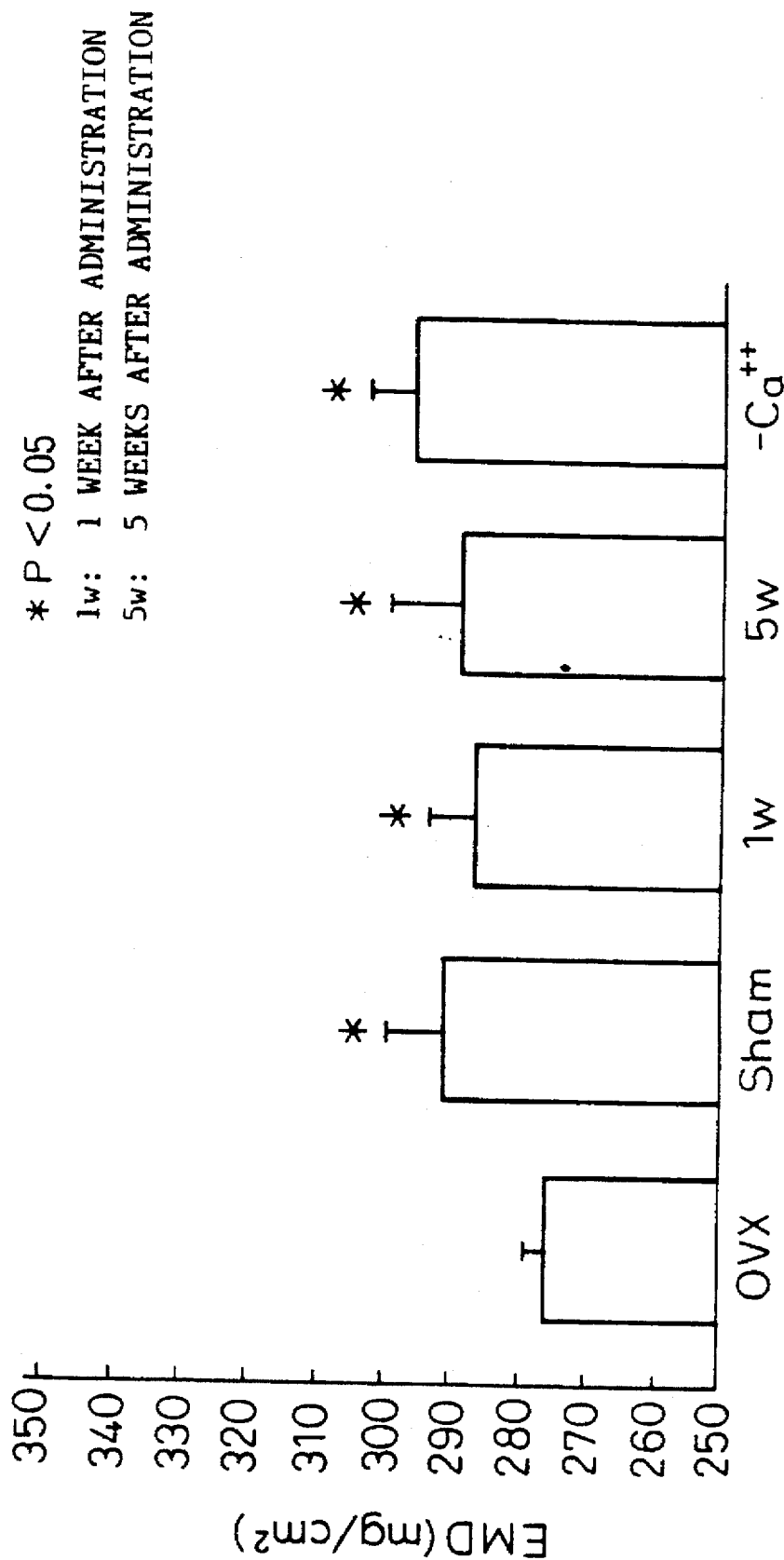

BONE RESORPTION INHIBITION/ OSTEOGENESIS PROMOTION PHARMACEUTICAL COMPOSITION

TECHNICAL FIELD

This invention relates to a pharmaceutical composition having novel bone resorption inhibition/osteogenesis promotion functions.

BACKGROUND ART

Normal retention of bones is accomplished by the balance of bone resorption and osteogenesis, and when bone resorption is promoted, bone components are dissolved and decrease, resulting in bone diseases such as osteoporosis. It is known that sex hormones such as estrogen have the function of suppressing bone resorption, and are therefore used as prophylactics and remedies for osteoporosis in Europe and America. Nonetheless, it has not yet been confirmed that these hormones concentrate in the bones, and the possibility of carcinogenesis resulting from single administration of these hormones cannot be denied.

On the other hand, tetracycline type antibiotics have a property such that they concentrate in the bones, but they have neither a bone resorption inhibition function nor an ossification function. Only U.S. Pat. No. 4,925,833 describes that tetracycline promotes the synthesis of bone proteins in the experiments at the cell level. Though synthesis of bone proteins is necessary for osteogenesis, the synthesis of bone proteins alone cannot promote osteogenesis.

Materials which have an osteogenesis promotion function and which can be used as the prophylactics and remedies for bone diseases are not yet known.

Accordingly, the present invention contemplates to provide a remedy for bone diseases which can provide a bone resorption inhibition function as well as osteogenesis function, preferably synergistically, and can concentrate in the bones.

DISCLOSURE OF THE INVENTION

The inventors of the present invention have conducted various studies to solve the problems described above and have found that the compounds which are obtained by causing a covalent bond between a tetracycline type antibiotic and asteroid type hormone such as estrogen, by a linker, has an osteogenesis function in addition to a bone resorption inhibition function and moreover, can concentrate in the bones, and have thus completed the present invention.

Accordingly, an active component of the present invention is represented by the formula (I):

$$X—Y—Z \quad (I)$$

[where X is a monovalent group represented by the following formula (II):

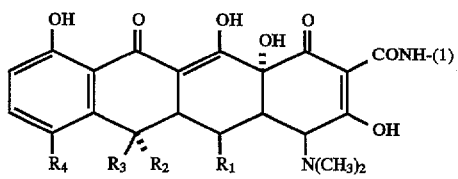

(where $R_1$ is hydrogen or a hydroxyl group, $R_2$ is hydrogen or a hydroxyl group, $R_3$ is hydrogen or a methyl group and $R_4$ is hydrogen, halogen or a dimethylamino group);

Y is a divalent or trivalent group represented by the following formula (III), (IV) or (V):

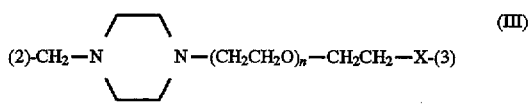

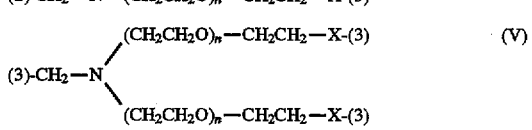

(where n is 0 to 4, and —X— is a direct bond, —O— or —NH—); and

Z is a monovalent group formed by removing hydrogen or a hydroxyl group from a compound represented by the following formula (VI):

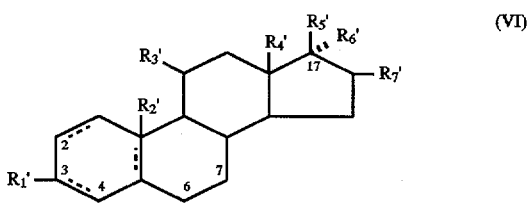

(where $R_1'$ is HO— or O=; $R_2'$ is a hydrogen atom or a methyl group; $R_3'$ is a hydrogen atom, a phenyl group or a substituted phenyl group; $R_4'$ is a methyl group or an ethyl group; $R_5'$ is a hydroxyl group, a ketone group or an acetyl group; $R_6'$ is hydrogen, a hydroxyl group, a methyl group, an ethynyl group or a prophynyl group; or $R_5'$ and $R_6'$ together form =O; $R_7'$ is hydrogen, a hydroxyl group or =O; or $R_6'$ and $R_7'$ are together bonded to oxygens of a 2,2-dioxypropyl group, and symbol ... represents a single bond or a double bond), whereby this bond group exists at the 2-position, 3-position, 4-position, 6-position, 7-position or 17-position, or at the phenyl group bonded to the 11-position, (1) of the formula (II) and (2) of the formulas (III) to (V) are directly connected, and (3) of the formulas (III) to (V) and any of the bond groups of the formula (VI) are directly bonded].

In the formula (II) described above, the halogen is, for example, fluorine, chlorine, bromine or iodine, and is preferably chlorine.

BRIEF DESCRIPTION OF THE DRAWINGS

FIGS. 1A to 3D show the results when the same experiment is repeatedly carried out three times.

FIG. 7 is a graph showing an effect of 0.5 mg/day of the compound 1-3 on the bone density (BMD) on DVX rats fed with high calcium feed.

BEST MODE FOR CARRYING OUT THE INVENTION

Figure 1A:
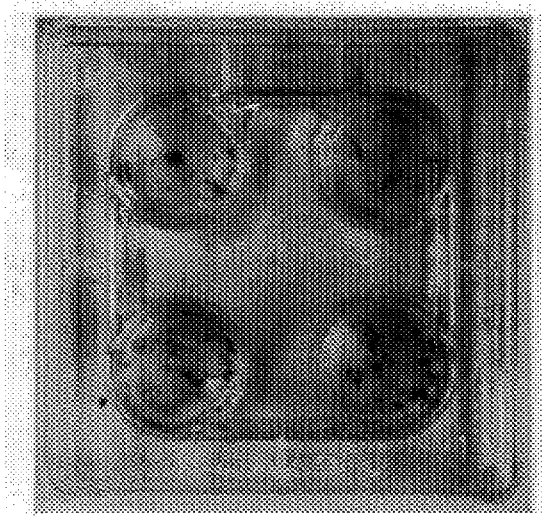
FIGS. 1A–1D are photographs showing the result of Experiment No. 3.
Figure 1B:
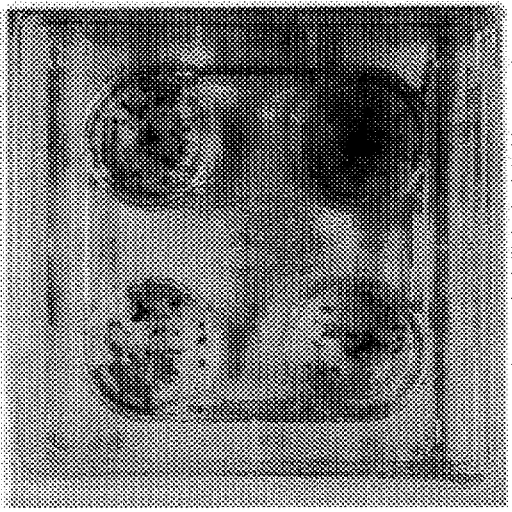
Figure 1C:
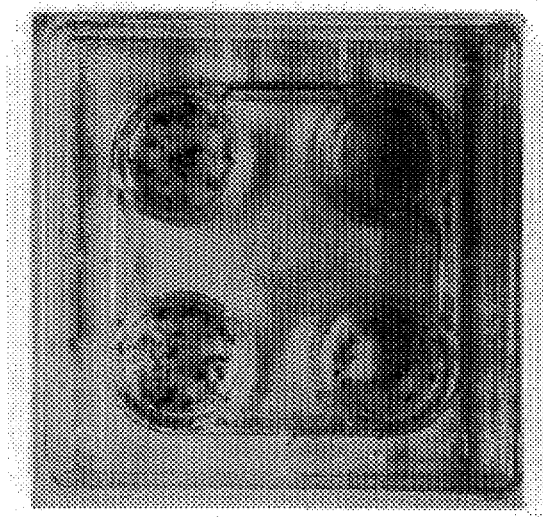
Figure 1D:
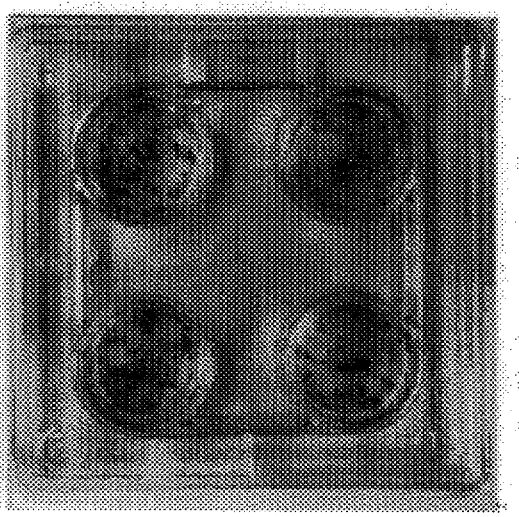
Figure 2A:
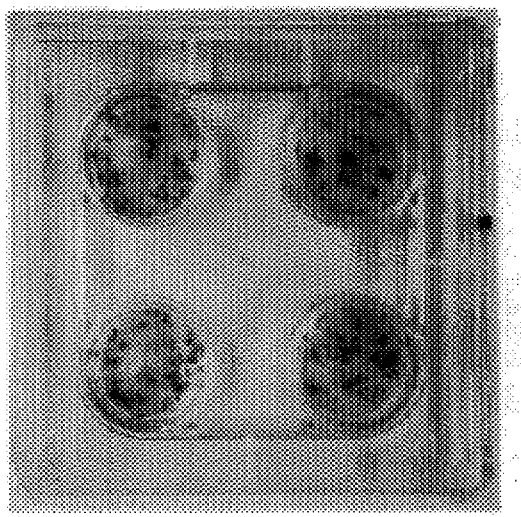
FIGS. 2A–2D are photographs showing the result of Experiment No. 3.
Figure 2B:
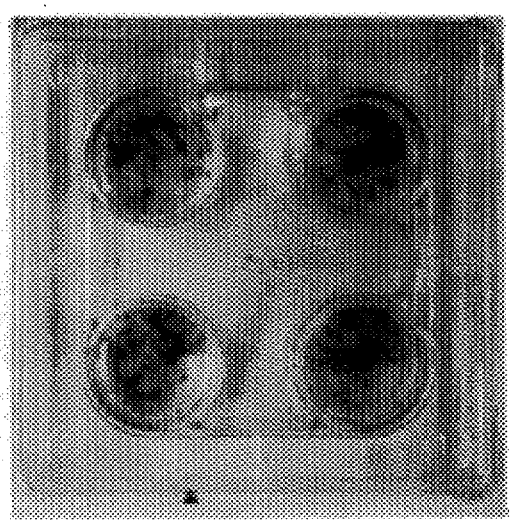
Figure 2C:
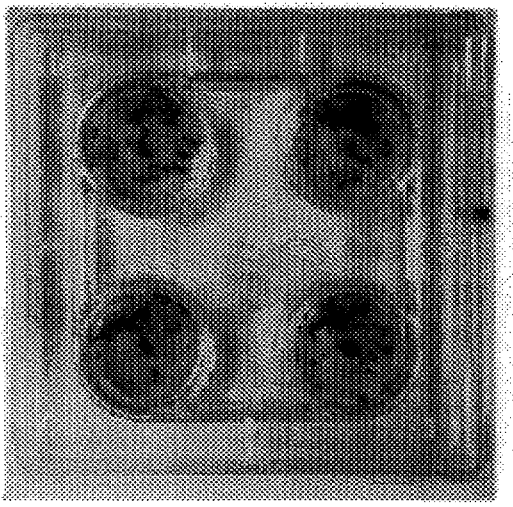
Figure 2D:
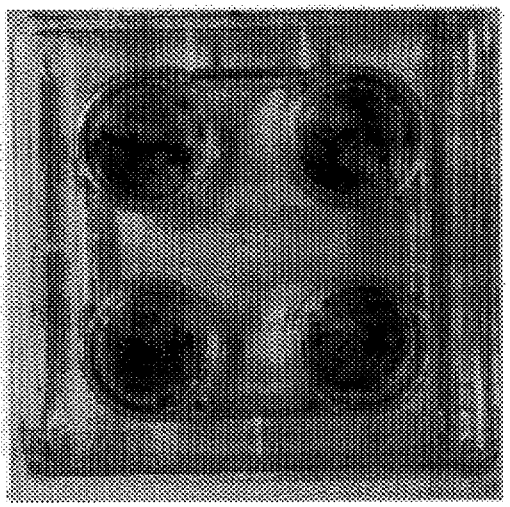
Figure 3A:
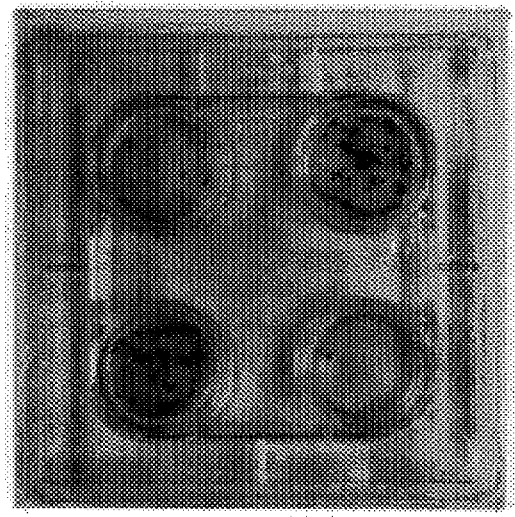
FIGS. 3A–3D are photographs showing the result of Experiment No. 3.
Figure 3B:
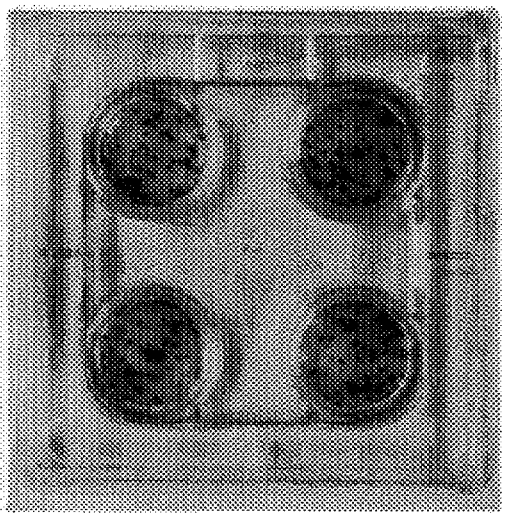
Figure 3C:
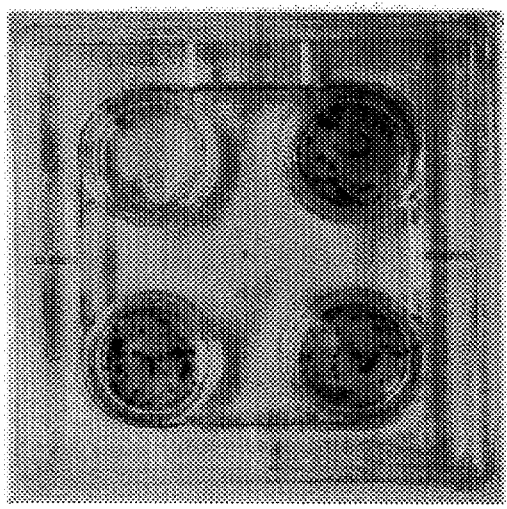
Figure 3D:
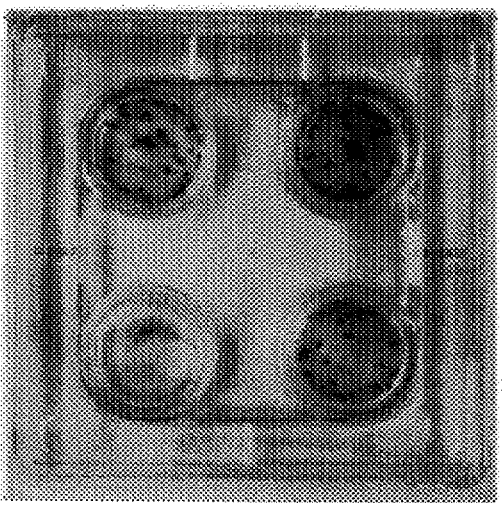

Examples of the monovalent group of the formula (II) which is a moiety of the compound of the formula (I) as the active ingredient of the pharmaceutical of the present invention are as follows:

Formula (II-1):

Monovalent group of tetracycline represented by the formula (II-1) (where, in the formula (II), $R_1$ is hydrogen, $R_2$ is a hydroxyl group, $R_3$ is a methyl group and $R_4$ is hydrogen):

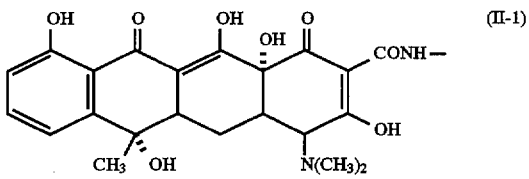

Formula (II-2):

Monovalent group of terramycin represented by the formula (II-2) (where, in the formula (II), $R_1$ is a hydroxyl group, $R_2$ is a hydroxyl group, $R_3$ is a methyl group and $R_4$ is a methyl group):

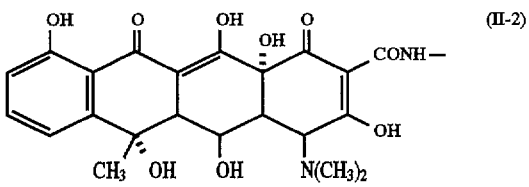

Formula (II-3):

Monovalent group of chlorotetracycline represented by the formula (II-3) (where, in the formula (II), $R_1$ is hydrogen, $R_2$ is a hydroxyl group, $R_3$ is a methyl group and $R_4$ is chlorine):

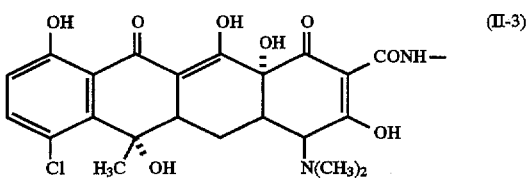

Formula (II-4):

Monovalent group of deoxytetracycline represented by the formula (II-4) (where, in the formula (II), $R_1$ is a hydroxyl group, $R_2$ is hydrogen, $R_3$ is a methyl group and $R_4$ is hydrogen):

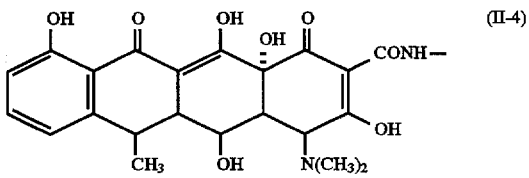

Formula (II-5):

Monovalent group of aminotetracycline represented by the formula (II-5) (where, in the formula (II), $R_1$ is hydrogen, $R_2$ is hydrogen, $R_3$ is hydrogen and $R_4$ is a dimethylamino group):

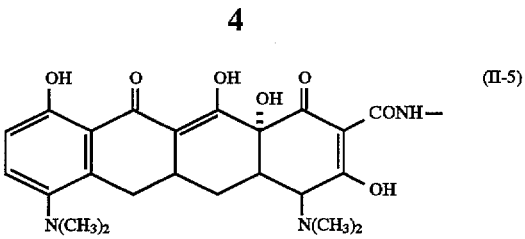

Examples of the monovalent groups of the compound of the formula (VI) which is a moiety of the compound of the formula (I) as the active ingredient of the pharmaceutical of the present invention are as follows.

Formula (VI-1):

Monovalent group of estron represented by the formula (VI-1) (where, in the formula (VI), $R_5'$ and $R_6'$ together form =O and $R_7'$ is hydrogen):

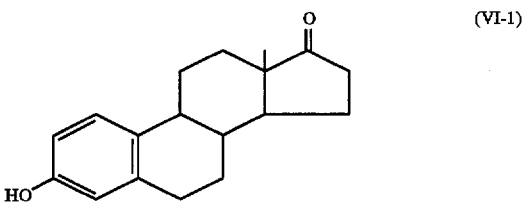

Formula (VI-2):

Monovalent group of estradiol represented by the formula (VI-2) (where, in the formula (I), $R_5'$ is a hydroxyl group, $R_6'$ is hydrogen and $R_7'$ is hydrogen):

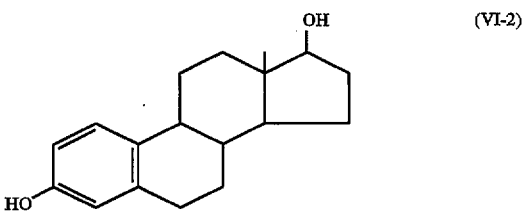

Formula (VI-3):

Monovalent group of estroalkynol represented by the formula (VI-3) (where, in the formula (VI), $R_5'$ is a hydroxyl group, $R_6'$ is an ethynyl group and $R_7'$ is hydrogen):

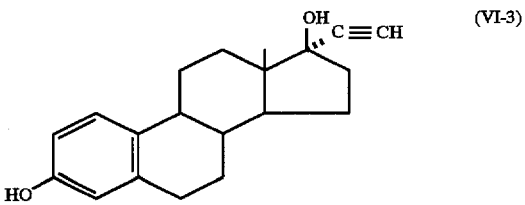

Formula (VI-4):

Monovalent group of estriol represented by the formula (VI-4) (where, in the formula (VI), $R_5'$ is a hydroxyl group, $R_6'$ is hydrogen and $R_7'$ is a hydroxyl group):

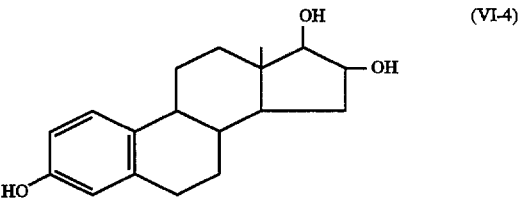

The bond group of the compounds of the formulas (VI) to (VI-4) described above exists at their 3-position, 6-position or 17-position.

The compound (VI) can further be those monovalent groups which are obtained by removing hydrogen or the hydroxyl group from the following compounds:
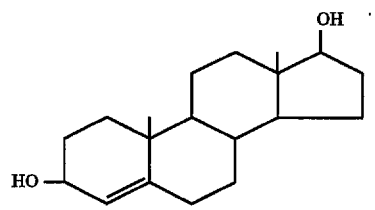
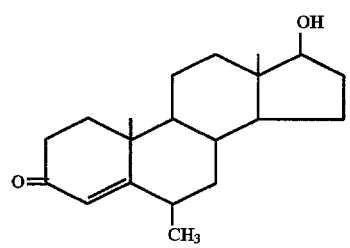
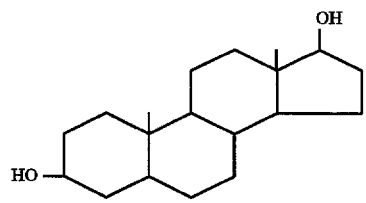
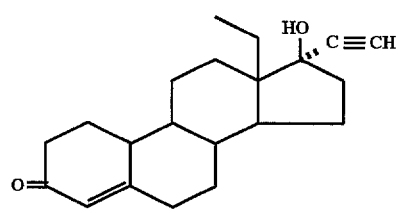
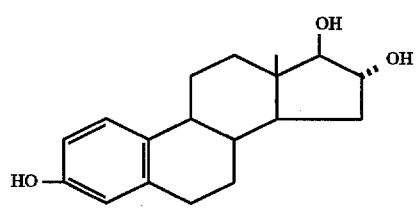
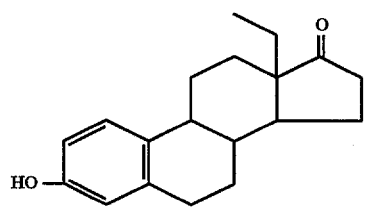
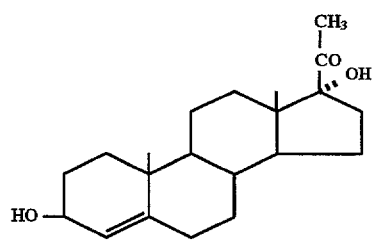
-continued
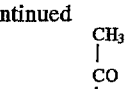
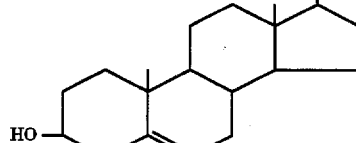
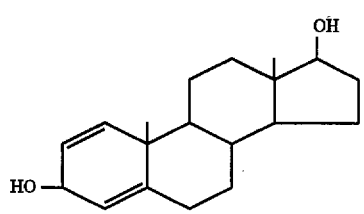
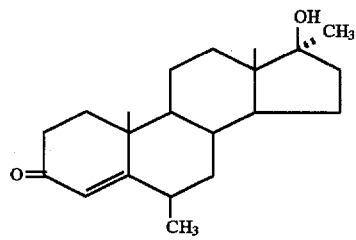
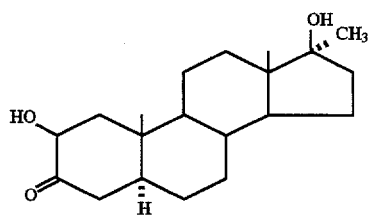
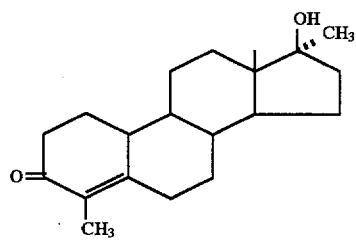
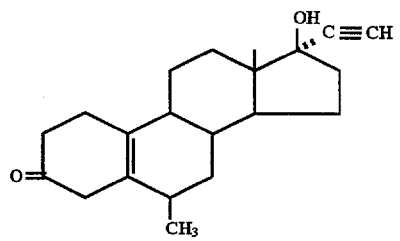
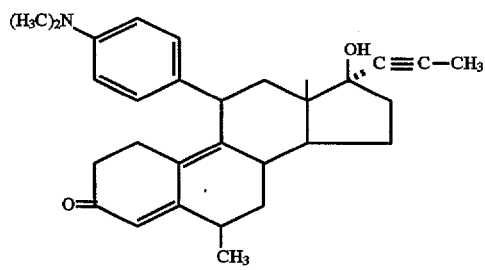

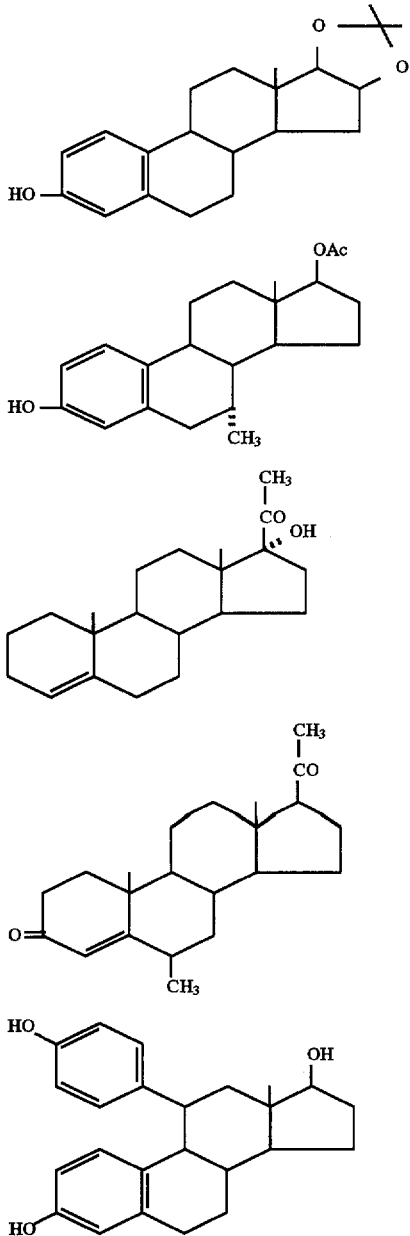

Accordingly, the active ingredient of the pharmaceutical of the present invention can be expressed by the following formulas, for example:

[II-1]—[III]—(3) [VI-1] (numeral in the parenthesis ( ) represents the position of the bond group of the group of the formula [VI-1]: hereinafter the same); [II-1]–[III]–(6) [VI-1], [II-1]–[III]–(17) [VI-1], [II-1]–[III]–(3) [VI-2], [II-1]–[III]–(6) [VI-2], [II-1]–[III]–(17) [VI-2], [II-1]–[III]–(3) [VI-3], [II-1]–[III]–(6) [VI-3], [II-1]–[III]–(17) [VI-3], [II-1]–[III]–(3) [VI-4], [II-1]–[III]–(6) [VI-4], [II-1]–[III]–(17) [VI-4],

[II-1]–[IV]–(3) [VI-1], [II-1]–[IV]–(6) [VI-1], [II-1]–[IV]–(17) [VI-1], [II-1]–[IV]–(3) [VI-2], [II-1]–[IV]–(6) [VI-2], [II-1]–[IV]–(17) [VI-2], [II-1]–[IV]–(3) [VI-3], [II-1]–[IV]–(6) [VI-3], [II-1]–[IV]–(17) [VI-3], [II-1]–[IV]–(3) [VI-4], [II-1]–[IV]–(6) [VI-4], [II-1]–[IV]–(17) [VI-4],

[II-1]–[V]–(3) [VI-1], [II-1]–[V]–(6) [VI-1], [II-1]–[V]–(17) [VI-1]; [II-1]–[V]–(3) [VI-2], [II-1]–[V]–(6) [VI-2], [II-1]–[V]–(17) [VI-2], [II-1]–[V]–(3) [VI-3], [II-1]–[V]–(6) [VI-3], [II-1]–[V]–(17) [VI-3], [II-1]–[V]–(3) [VI-4], [II-1]–[V]–(6) [VI-4], [II-1]–[V]–(17) [VI-4],

[II-2]–[III]–(3) [VI-1], [II-2]–[III]–(6) [VI-1], [II-2]–[III]–(17) [VI-1], [II-2]–[III]–(3) [VI-2], [II-2]–[III]–(6) [VI-2], [II-2]–[III]–(17) [VI-2], [II-2]–[III]–(3) [VI-3], [II-2]–[III]–(6) [VI-3], [II-2]–[III]–(17) [VI-3], [II-2]–[III]–(3) [VI-4], [II-2]–[III]–(6) [VI-4], [II-2]–[III]–(17) [VI-4],

[II-2]–[IV]–(3) [VI-1], [II-2]–[IV]–(6) [VI-1], [II-2]–[IV]–(17) [VI-1], [II-2]–[IV]–(3) [VI-2], [II-2]–[IV]–(6) [VI-2], [II-2]–[IV]–(17) [VI-2], [II-2]–[IV]–(3) [VI-3], [II-2]–[IV]–(6) [VI-3], [II-2]–[IV]–(17) [VI-3], [II-2]–[IV]–(3) [VI-4], [II-2]–[IV]–(6) [VI-4], [II-2]–[IV]–(17) [VI-4],

[II-2]–[V]–(3) [VI-1], [II-2]–[V]–(6) [VI-1], [II-2]–[V]–(17) [VI-1], [II-2]–[V]–(3) [VI-2], [II-2]–[V]–(6) [VI-2], [II-2]–[V]–(17) [VI-2], [II-2]–[V]–(3) [VI-3], [II-2]–[V]–(6) [VI-3], [II-2]–[V]–(17) [VI-3], [II-2]–[V]–(3) [VI-4], [II-2]–[V]–(6) [VI-4], [II-2]–[V]–(17) [VI-4],

[II-3]–[III]–(3) [VI-1], [II-3]–[III]–(6) [VI-1], [II-3]–[III]–(17) [VI-1], [II-3]–[III]–(3) [VI-2], [II-3]–[III]–(6) [VI-2], [II-3]–[III]–(17) [VI-2], [II-3]–[III]–(3) [VI-3], [II-3][III]–(6) [VI-3], [II-3]–[III]–(17) [VI-3], [II3]–[III]–(3) [VI-4], [II-3] [III]–(6) [VI-4], [II-3]–[III]–(17) [VI-4],

[II-3]–[IV]–(3) [VI-1], [II-3]–[IV]–(6) [VI-1], [II-3]–[IV]–(17) [VI-1], [II-3]–[IV]–(3) [VI-2], [II-3]–[IV]–(6) [VI-2], [II-3]–[IV]–(17) [VI-2], [II-3]–[IV]–(3) [VI-3], [II-3]–[IV]–(6) [VI-3], [II-3]–[IV]–(17) [VI-3], [II-3]–[IV]–(3) [VI-4], [II-3]–[IV]–(6) [VI-4], [II-3]–[IV]–(17) [VI-4],

[II-3]–[V]–(3) [VI-1], [II-3]–[V]–(6) [VI-1], [II-3]–[V]–(17) [VI-1], [II-3]–[V]–(3) [VI-2], [II-3]–[V]–(6) [VI2], [II-3]–[V]–(17) [VI-2], [II-3]–[V]–(3) [VI-3], [II-3]–[V]–(6) [VI-3], [II-3]–[V]–(17) [VI-3], [II-3]–[V]–(3) [VI-4], [II-3]–[V]–(6) [VI-4], [II-3]–[V]–(17) [VI-4],

[II-4]–[III]–(3) [VI-1], [II-4]–[III]–(6) [VI-1], [II-4]–[III]–(17) [VI-1], [II-4]–[III]–(3) [VI-2], [II-4]–[III]–(6) [VI-2], [II-4]–[III]–(17) [VI-2], [II-4]–[III]–(3) [VI-3], [II-4]–[III]–(6) [VI-3], [II-4]–[III]–(17) [VI-3], [II-4]–[III]–(3) [VI-4], [II-4]–[III]–(6) [VI-4], [II-4]–[III]–(17) [VI-4],

[II-4]–[IV]–(3) [VI-1], [II-4]–[IV]–(6) [VI-1], [II-4]–[IV]–(17) [VI-1], [II-4]–[IV]–(3) [VI-2], [II-4]–[IV]–(6) [VI-2], [II-4]–[IV]–(17) [VI-2], [II-4]–[IV]–(3) [VI-3], [II-4]–[IV]–(6) [VI-3], [II-4]–[IV]–(17) [VI-3], [II-4]–[IV]–(3) [VI-4, [II-4]–[IV]–(6) [VI-4], [II-4]–[IV]–(17) [VI-4],

[II-4]–[V]–(3) [VI-1], [II-4]–[V]–(6) [VI-1], [II-4]–[V]–(17) [VI-1], [II-4]–[V]–(3) [VI-2], [II-4]–[V]–(6) [VI-2], [II-4]–[V]–(17) [VI-2], [II-4]–[V]–(3) [VI-3], [II-4]–[V]–(6) [VI-3], [II-4]–[V]–(17) [VI-3], [II-4]–[V]–(3) [VI-4], [II-4]–[V]–(6) [VI-4], [II-4]–[V]–(17) [VI-4],

[II-5]–[III]–(3) [VI-1], [II-5]–[III]–(6) [VI-1], [II-5]–[III]–(17) [VI-1], [II-5]–[III]–(3) [VI-2], [II-5]–[III]–(6) [VI-2], [II-5]–[III]–(17) [VI-2], [II-5]–[III]–(3) [VI-3], [II-5]–[III]–(6) [VI-3], [II-5]–[III]–(17) [VI-3], [II-5]–[III]–(3) [VI-4], [II5]–[III]–(6) [VI-4], [II-5]–[III]–(17) [VI-4],

[II-5]-[IV]-(3) [VI-1], [II-5]-[IV]-(6) [VI-1], [II-5]-[IV]-(17) [VI-1], [II-5]-[IV]-(3) [VI-2], [II-5]-[IV]-(6) [VI-2], [II-5]-[IV]-(17) [VI-2], [II-5]-[IV]-(3) [VI-3], [II-5]-[IV]-(6) [VI-3], [II-5]-[IV]-(17) [VI-3], [II-5]-[IV]-(3) [VI-4], [II-5]-[IV]-(6) [VI-4], [II-5]-[IV]-(17) [VI-4],

[II-5]-[V]-(3) [VI-1], [II-5]-[V]-(6) [VI-1], [II-5]-[V]-(17) [VI-1], [II-5]-[V]-(3) [VI-2], [II-5]-[V]-(6) [VI-2], [II-5]-[V]-(17) [VI-2], [II-5]-[V]-(3) [VI-3], [II-5]-[V]-(6) [VI-3], [II-5]-[V]-(17) [VI-3], [II-5]-[V]-(3) [VI-4], [II-5]-[V]-(6) [VI-4], [II-5]-[V]-(17) [VI-4].

The compounds per se described above can be prepared by the known methods. For example, the linker represented by the formulas (III) to (V) is first bonded to the steroid compound represented by the formula (VI), and then the resulting bond product is bonded to the tetracycline type material.

Bonding of the linker of the formulas (III) to (V) to the 3-position of the steroid compound of the formula (VI) is carried out in accordance with the following reaction formula, for example:

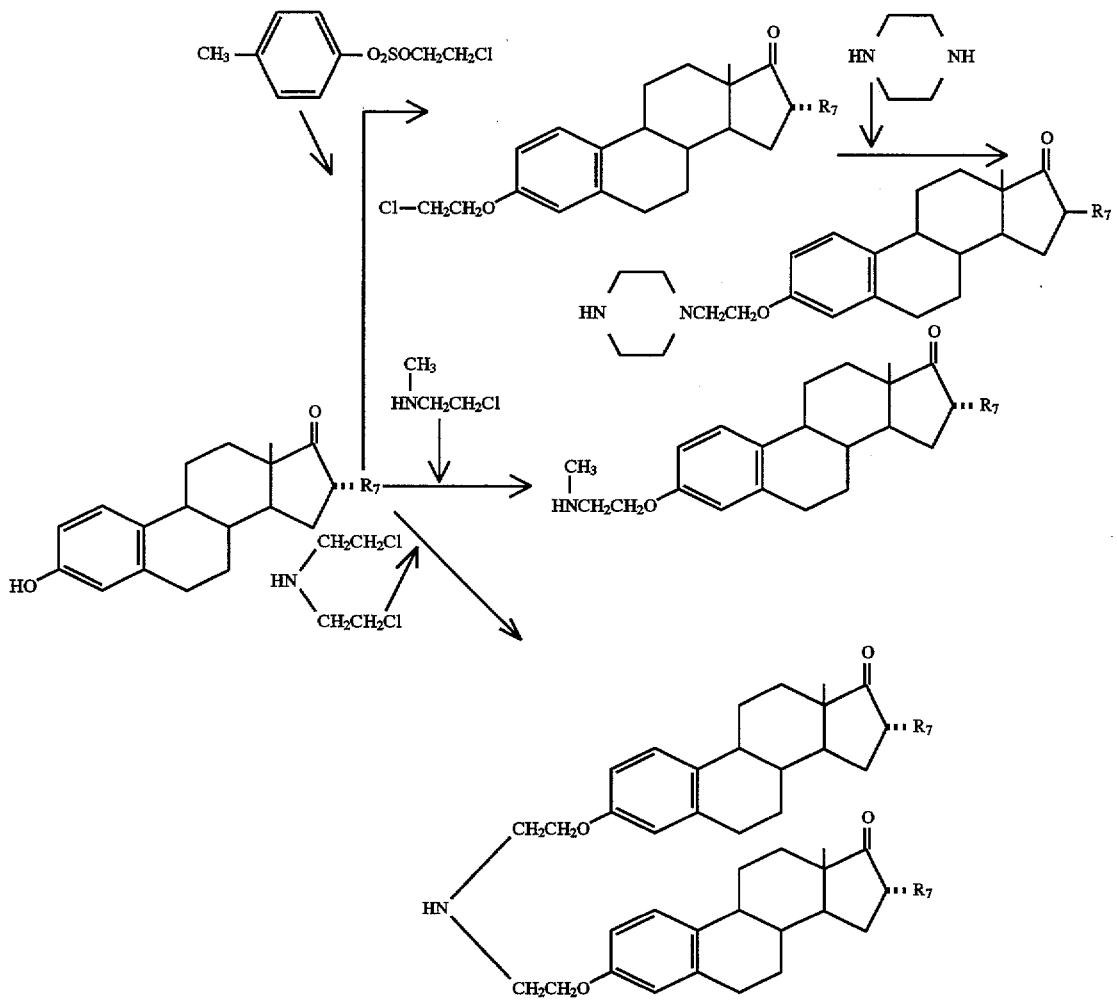

Further, the compound in which $R_5'$ is a hydroxyl group and $R_6'$ is hydrogen or an ethynyl group can be obtained by the following reaction, for example:

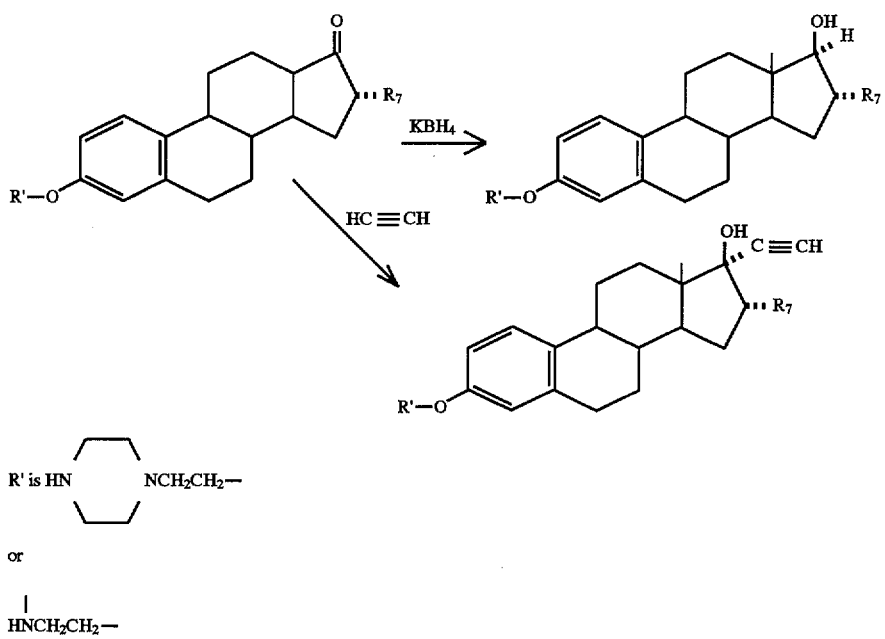

To bond the linker of the formulas (III) to (V) to the 6-position of the steroid compound represented by the formula (VI), an =O group is first introduced into the 6position of the steroid compound and then, the following reaction may be carried out:

pound by cross-linking the N atom of the linker with the N atom of the amide group of the tetracycline compound by formaldehyde.

The pharmaceutical according to the present invention can be dosed by peroral or parenteral administration such as

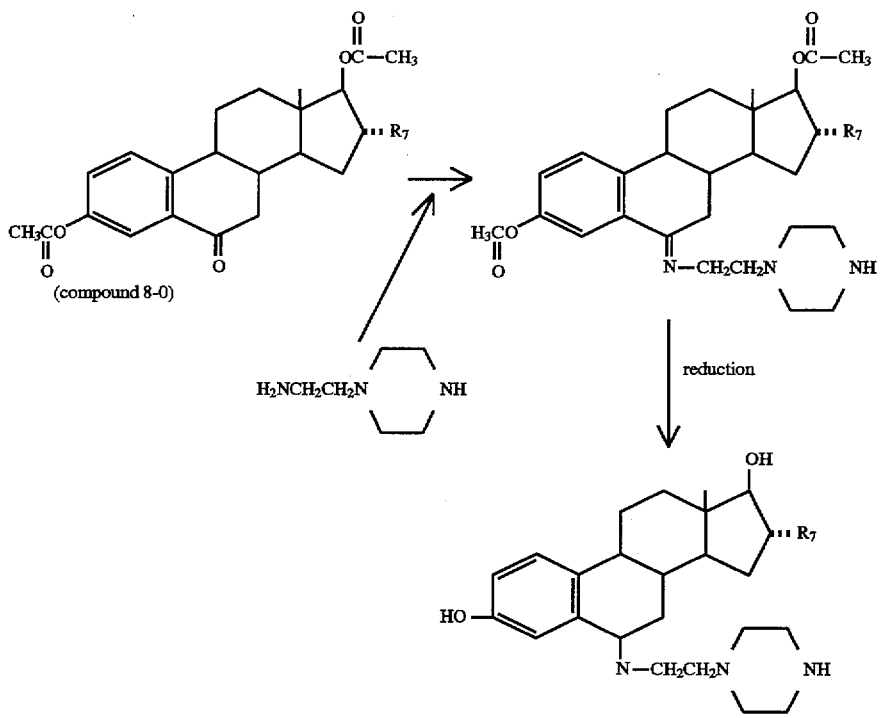

Next, the tetracycline compound can be bonded to the reaction product between the linker and the steroid comphleboclysis, hyperdermic injection, intramuscular injection, intra-abdominal injection, and so forth. An effective daily dosage to man is from 0.2 to 200 mg in peroral administration and from 0.1 to 100 mg in parenteral administration. The compound of the present invention has extremely low toxicity, and an $LD_{50}$ in peroral administration of the compound 1 prepared in Example 1, for example, in mice is about 143 mg/kg.

The pharmaceutical of the present invention can take customary forms of preparations in accordance with the route of administration. In the case of peroral administration, for example, the pharmaceutical can take the forms of a capsule, a tablet, a granule, powder, a liquid preparation, and so forth. They can be prepared in a customary manner. The liquid preparation, for example, can be prepared by dissolving or suspending the active ingredient of the present invention in an appropriate medium such as an aqueous buffer, or the like. The powder preparation can be prepared by mixing the active ingredient of the present invention with a powdery filler such as a starch, e.g. corn starch, and/or a saccharide such as lactose.

The tablet is prepared by mixing the active ingredient with the filler, such as the filler described above, and a binder such as starch paste, and compressing the mixture by a tableting machine. The granule can be prepared by mixing the active ingredient with the filler, the binder, etc., kneading the mixture with a liquid such as water and/or glycerine, passing the resulting product through a sieve to granulate it and drying the resulting granules. The capsule can be prepared by encapsulating the powder or the granules described above in a capsule having a suitable size.

elementary analysis: C 72.40, H 43, Cl 10.71

Synthesis of 1-2.N-[17-oxy-estra-1,3,5 (10)-trien-3-oxyethyl]piperazine (Compound 1-2):

7.8 g of the compound (1-1) described above, 46.6 g of anhydrous piperazine and 120 ml of dimethyl formamide (DMF) were reacted at 80° to 100° C. for 5 hours. After the DMF was evaporated and removed, the resulting solid matter was again recrystallized from alcohol and acetone so as to obtain a white crystalline compound (VI). The yield was 85%.

m.p.=140° to 142° C.

elementary analysis: C 75.10, H 9.20, N 7.40

Synthesis of 1-3.N-4-[17-oxy-estra-1,3,5 (10)-trien-3-oxyethyl]-piperazine-1-methylene-tetracycline (Compound 1-3):

3.8 g of the compound (1-2) described above, 0.03 g of metaformaldehyde and 15 ml of isopropanol were reacted at 40° C. for 2 hours. After 3.5 g of tetracycline was added, the mixture was stirred and reacted for 5 hours. After the reaction was completed, the reaction product was filtrated and was washed with isopropanol and ethyl ether. Thereafter, a yellow solid matter (compound 1-3) was obtained ($R_1=R_4=H$, $R_2=OH$, $R_3=CH_3$). The yield was 95%.

m.p.=160° C. (dec)

elementary analysis: C 67.21, H 7.12, N 6.67

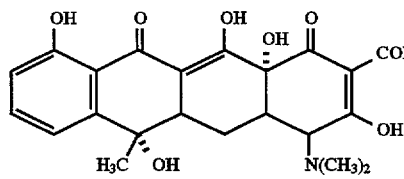
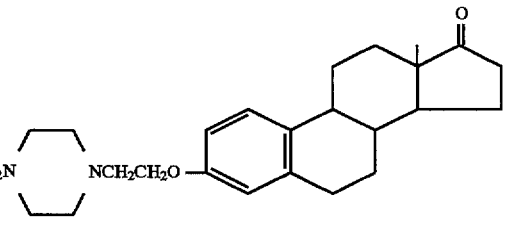

The parenteral dosages can be prepared by dissolving or suspending the active ingredient in physiological saline solution or a buffer such as a phosphoric acid buffer, for example. The parenteral dosages may be freeze-dried products which are to be dissolved or suspended before use, and supports for freeze-drying may be saccharides such as lactose, or customary freeze-dry supports.

EXAMPLES

Hereinafter, concrete examples of the compounds according to the present invention will be described. However, the primary scope of the present invention is not limited to these examples.

Synthesis Example 1

Synthesis of 1-1.3-chloroethoxy-17-oxyestra-1,3,5 (10)-trien (Compound 1-1):

A NaOH solution was added to a toluene solution prepared by mixing 27.1 g of estrone, 22.2 g of 3-chloroethoxy-17-oxyestra-1,3,5 (10)-trien and a small amount of triethylaniline chloride. After a pH was adjusted to about 10, the reaction was carried out for 4 hours and the solvent was evaporated. The solid matter was recrystallized from alcohol, and a compound (1-1, $R_7=H$) was obtained. The yield was 79%.

m.p.=86° to 88° C.

Synthesis Example 2

2-1. Synthesis of 2-1.N-[17β-hydroxy-estra-1,3,5 (10)-trien-3-oxyethyl]piperazine (Compound 2-1):

3.8 g of the compound (1-2) of Example 1 was dissolved in methyl alcohol. After 0.5 g of potassium borohydrate was added under an alkaline condition, the reaction mixture was reacted under heating and turning flow for 3 hours. The reaction solution was neutralized by an acid and methyl alcohol was evaporated. The resulting solid component was recrystallized from alcohol. Finally, a white crystal (compound 2-1, $R_7=H$) was obtained. The yield was 91%.

m.p.=141° to 142° C.

elementary analysis: C 75.21, H 9.23, N 7.14

2-2. Synthesis of N-4-[17β-hydroxy-estra-1,3,5 (10)-trien-3-oxyethyl]-piperazine-1-methylene-tetracycline (Compound 2-2):

3.84 g of the compound (2-1) described above, 0.03 g of metaformaldehyde and 20 ml of isopropanol were reacted at 40° C. for 2 hours. After 3.5 g of tetracycline was added, the reaction mixture was stirred and reacted for 5 hours. After the reaction was completed, the reaction product was filtrated and was washed with isopropanol and ethyl ether. Thereafter, a pale yellow solid matter (compound 2-2) ($R_1=R_4=H$, $R_2=OH$, $R_3=CH_3$) was obtained. The yield was 95%.

m.p.=165° C. (dec)

elementary analysis: C 67.30, H 7.34, N 6.54

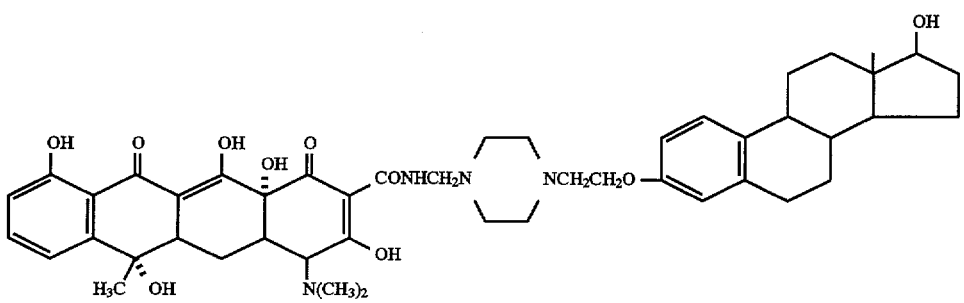

Synthesis Example 3

Synthesis of N-4-[17β-hydroxy-estra-1,3,5 (10)-trien-3-oxyethyl]1-piperazine-1-methylene-oxytetracycline (Compound 3-1):

3.8 g of the compound of Example 2 (2-1), 0.03 g of metaformaldehyde and 20 ml of isopropanol were reacted at 40° C. for 2 hours. After 3.5 g of tetramycine was added, the reaction mixture was stirred and reacted for 5 hours. After the reaction was completed, the treatment was carried out in the same way as in Example 1-3, and a pale yellow solid matter (compound 3) ($R_1=R_2=OH$, $R_3=CH_3$, $R_4=H$) was obtained. The yield was 93%.

m.p.=171° C. (dec)

elementary analysis: C 65.62, H 7.10, N 6.67 water and toluene with stirring. After the mixed solution was subjected to refluxing for 5 hours, the solvent was evaporated. The solid content was recrystallized from alcohol, and the intended product was obtained. The yield was 72%.

m.p.=256° to 259° C.

elementary analysis: C 78.50, H 8.60, N 2.31

4-2. Synthesis of bis-N,N-[17-oxy-estra-1,3,5 (10)-trien-3-oxyethyl]aminomethylene-tetracycline (Compound 4-2):

6.1 g of the compound (4-1) described above, 0.03 g of metaformaldehyde and 20 ml of isopropanol were reacted at 40° C. for 2 hours. After 3.5 g of tetracycline was added, the reaction mixture was stirred and reacted for 8 hours. After the reaction was completed, a pale yellow solid matter (compound 4-2) ($R_1=R_4=H$, $R_2=OH$, $R_3=CH_3$) was obtained. The yield was 68%.

m.p.=183° C. (dec)

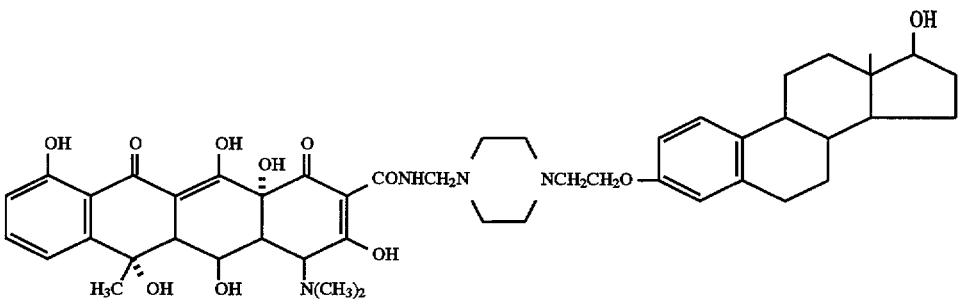

Synthesis Example 4

4-1. Synthesis of bis-N,N-[17-oxy-estra-1,3,5 (10)-trien-3-oxyethyl]amine (Compound 4-1)

A NaOH solution was added to a mixture of 3.6 g of mastagen chloride, 12 g of estron, 4 g of triethyl aniline, elementary analysis: C 71.10, H 7.21, N 3.89

The structure was represented by the following molecular formula:

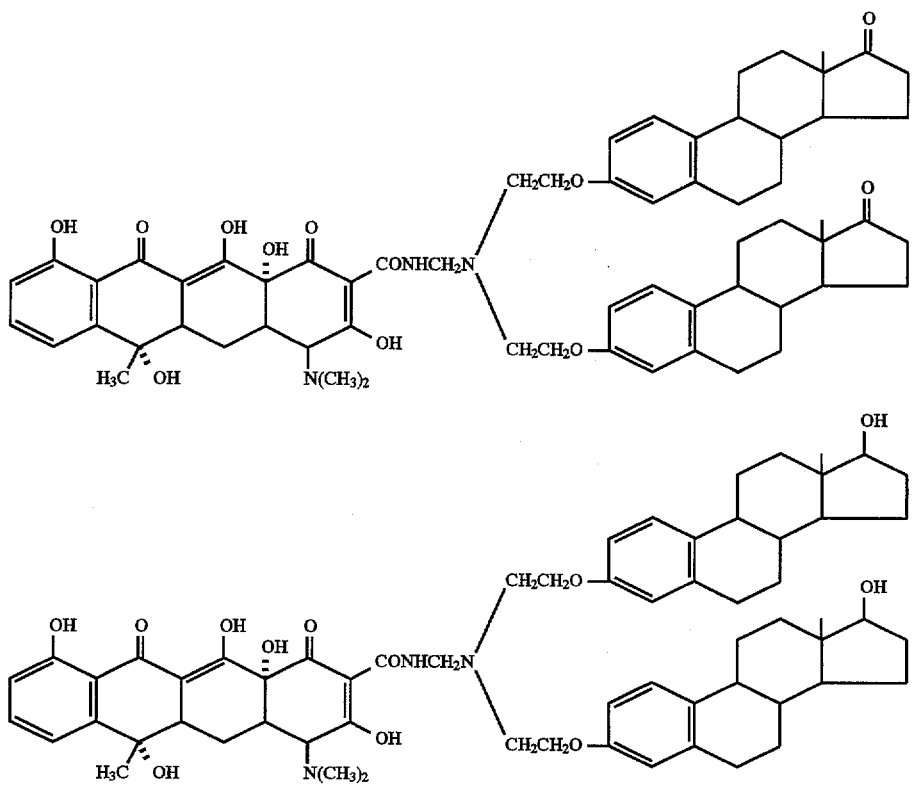

Synthesis Example 5

5-1. Synthesis of bis-N,N-[17β-hydroxy-estra-1,3,5 (10)-trien-3-oxyethyl]amine (Compound 5-1):

Methyl alcohol was added to 6.1 g of the compound (4-1) described above, and after 0.5 g of potassium borohydrate was added under an alkaline condition, the reaction was carried out under refluxing for 5 hours. Next, the reaction solution was neutralized by an acid and methyl alcohol was evaporated. The solid matter was refined in an acetone solution and an alcohol solution. Estron-17-ketone in the resulting compound (4-1) was reduced to a white product having the −17β-hydroxyl group. The yield was 82%.

m.p.=193° to 197° C.

elementary analysis: C 78.41, H 8.51, N 2.33

5-2. Synthesis of bis-N,N-[17β-hydroxy-estra-1,3,5 (10)-trien-3-oxyethyl]aminomethylene-tetracycline (Compound 5-2):

5.4 g of the compound (5-1) described above, 0.03 g of metaformaldehyde and 20 ml of isopropanol were reacted at 40° C. for 2 hours. After 3.5 g of tetracycline was added, the reaction mixture was stirred and reacted for 8 hours. After the reaction was completed, a pale yellow solid matter (compound 5-2) ($R_1=R_4=H$, $R_2=OH$, $R_3=CH_3$) was obtained in the saml way as in Example 1-3. The yield was 94%.

m.p.=171° C. (dec)

elementary analysis: C 71.02, H 7.02, N 3.98

The structure was represented by the following molecular formula:

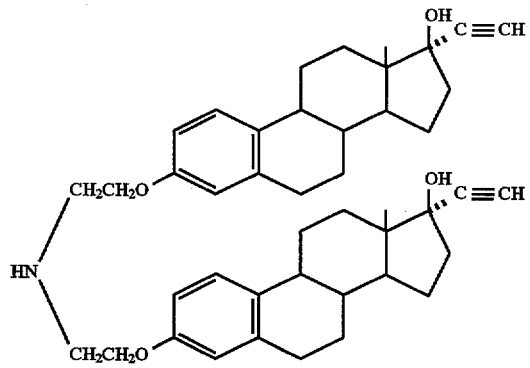

Synthesis Example 6

6-1. Synthesis of bis-N,N-[17β-hydroxy-17α-ethynyl-estra-1,3,5 (10)-trien-3-oxyethyl]amine (Compound 6-1):

6.1 g of the compound (4-1) of Example 4 was dissolved in 100 ml of tetrahydrofuran and 1.0 g of potassium hydroxide powder, and the mixture was completely reacted at 0° C. with vigorous stirring by introducing an acetylene gas. The reaction mixture was neutralized to pH 4 by an acid and the solvent was evaporated. The reaction product was then washed with water and was dried. It was further recrystallized from alcohol and chloroform, and a white solid matter (6-1) was obtained. The yield was 78%.

m.p.=201° to 205° C.

elementary analysis: C 79.21, H 8.58, N 2.18

The structure was expressed by the following molecular formula:

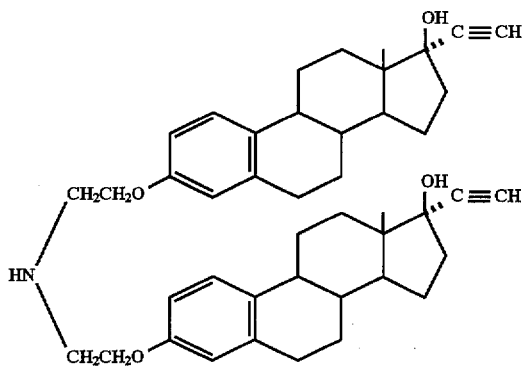

6-2.6. 6 g of the compound (6-1) described above, 0.03 g of metaformaldehyde and 20 ml of isopropanol were reacted at 60° C. for 2 hours and then 3.4 g of tetracycline was added. The reaction mixture was stirred and reacted for 8 hours. After the reaction was completed, a pale yellow solid matter (compound 6-2), i.e., bis-N,N-[17β-hydroxy-17α-ethynyl-estra-1,3,5 (10)-trien-3-oxyethyl]aminomethylene-tetracycline ($R_1=R_4=H$, $R_2=OH$, $R_3=CH_3$) was obtained in the saml way as Example 1–3. The yield was 93%.

m.p.=178° C. (dec)

elementary analysis: C. 72.1, H 7.12, N 3.90

The structure was represented by the following molecular formula:

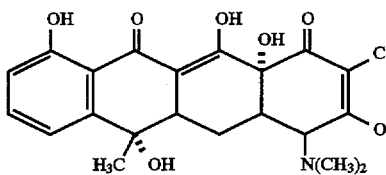

Synthesis Example 7

7-1. Synthesis of N-[17-oxy-estra-1,3,5 (10)-trien-3-oxyethyl]-N-methylamine (Compound 7-1):

2.7 g of estron, 1 g of chloroethylmethylamine and a small amount of triethylaniline were mixed with a toluene solution, and a sodium hydroxide solution was added. After the pH was adjusted to about 10, the reaction mixture was reacted for 4 hours. Thereafter, the solvent was evaporated, and the solid matter was recrystallized from alcohol to obtain a compound (7-1, $R_7=H$). The yield was 71%.

m.p.=262° to 266° C.

elementary analysis: C 75.24, H 9.41, N 4.28

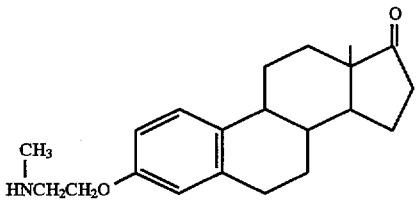

7-2. 3.3 g of the compound (7-1) described above, 0.03 g of metaformaldehyde and 20 ml of isopropanol were reacted at 60° C. for 2 hours and then 3.5 g of tetracycline was added. The reaction mixture was stirred and reacted for 8 hours. After the reaction was completed, a pale yellow solid matter (compound 7-2), i.e., N-[17-oxy-estra-1,3,5 (10)-trien-3-oxyethyl]-N-methylaminomethylene-tetracycline ($R_1=R_4=H$, $R_2=OH$, $R_3=CH_3$) was obtained in the saml way as in Example 1–3. The yield was 90%.

m.p.=190° C. (dec)

elementary analysis: C. 68.8, H 7.22, N 3.62

The structure was expressed by the following molecular formula:

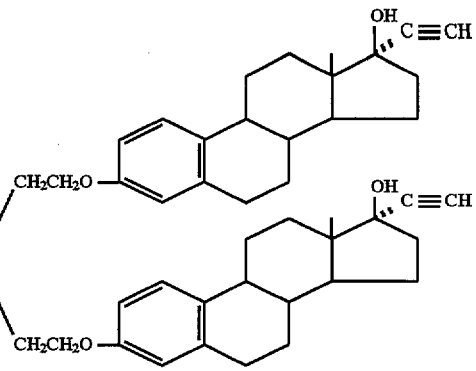

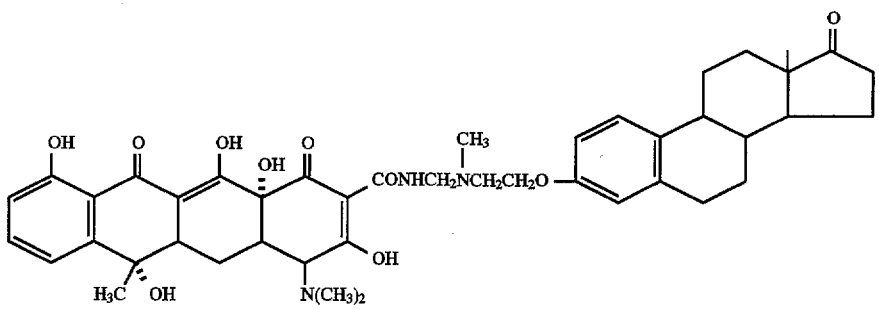

Synthesis Example 8

8-1. Synthesis of N-[3,17β-dihydroxy-estra-1,3,5 (10)-trien-6-aminoethyl]piperazine (Compound 8-1):

5.2 g of the compound (8-0) was dissolved in 120 ml of tetrahydrofuran, and 3.2 g of aminoethyl piperazine was added. The reaction mixture was subjected to refluxing and was reacted for 2 hours. THF was evaporated and removed, and 100 ml of methyl alcohol and 2.8 g of formic acid were added. Refluxing was further carried out, and the reaction mixture was reacted for hours. Methyl alcohol was evaporated and removed, and the residue was recrystallized from alcohol to obtain a compound 8-1.

m.p.=172° to 177° C.

8-2. Synthesis of N-4-(3,17β-dihydroxy-estra-1,3,5 (10)-trien-6-aminoethyl]-piperazine-1-methylene-tetracycline (Compound 8-2):

4.1 g of the compound (8-1) described above, 0.03 g of metaformaldehyde and 20 ml of isopropanol were mixed and were reacted at 50° C. for 2 hours. After 3.5 g of tetracycline was added, the reaction mixture was stirred and reacted for 5 hours. After the reaction was completed, the reaction product was filtrated, was washed with isopropanol and ethyl ether, and was dried in vacuum to obtain a pale yellow solid matter (compound 8-2). The melting point was 167° C. (dec) and the yield was 81.2%.

reaction solution was neutralized by dilute acetic acid to neutrality, and was then diluted by water. After the solid matter was so formed, it was filtrated, was washed with water and was dried. The product was recrystallized from water-containing alcohol to obtain a white crystal. The melting point was 173° to 174° C. and the yield was 97.2%.

2. Preparation of 17β-estroalkynol diacetate 10 g of 17β-estroalkynol was dissolved in pyritein and 35 ml of acetic acid was added thereto. The reaction mixture was reacted under refluxing for one hour and was poured into ice water to form a solid matter. The resulting solid was filtrated and dried, and the reaction product was recrystallized from absolute alcohol to obtain white crystals. The melting point was 126° to 128° C. and the yield was 97%.

3. Preparation of 6-carbonyl-17β-estroalkynol diacetate (Compound (XII))

5 g of 17β-estroalkynol diacetate was dissolved in benzene, and 0.45 g of chromium trioxide was added dropwise under a cooled state, and the mixture was then dissolved in a mixed benzene solution of 30 ml of glacial acetic acid, 20 ml of acetic acid and 30 ml of benzene. After the reaction was completed, the reaction was stirred for a while and was then poured into water. The reaction product was extracted with ethyl ether, was washed with a saturated sodium hydrogencarbonate solution, then with water, was dried and concentrated, and was thereafter separated by

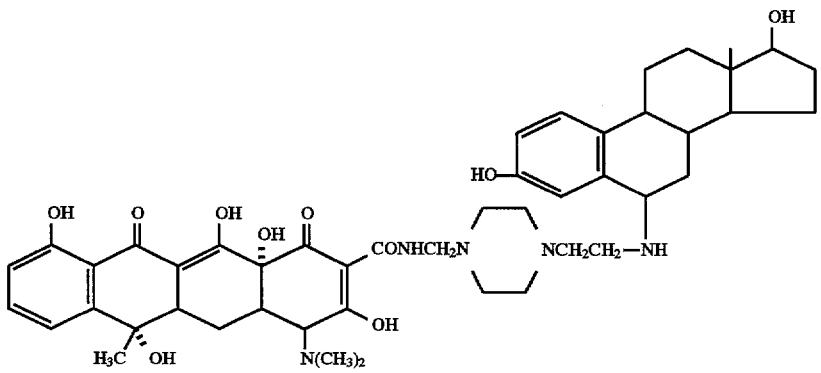

The compound (8-0) was produced in the following manner.

1. Preparation of 17β-estroalkynol 4 g of estron was dissolved in methyl alcohol, and a mixed solution of 0.8 g of potassium borohydrate, 1.76 g of sodium hydroxide and 8.8 ml of water was added dropwise at about 30° C. Thereafter, the reaction was carried out for 2 hours, and the silica gel to obtain a product. The melting point was 173° to 175° C. and the yield was 40%.

Synthesis Example 9

Synthesis of N-4-[17-oxy-estra-1,3,5 (10)-trien-3-oxyethyl]-1-piperazine-1-methylene-doxycycline HCl (Compound 9):

2.2 g of the compound (1-2), 0.20 g of polyformaldehyde and 100 ml of isopropanol were heated and stirred at 60° C. for 1.5 hours, and 3 g of doxycycline hydrochloride was added. The reaction mixture was kept at 60° C. and was stirred for 2.5 hours. After the reaction was completed, the reaction product was filtrated, was washed with isopropanol and ethyl ether and was dried to obtain a pale yellow solid matter (compound 9) having a melting point of 172° C. (dec.). The yield was 87%.

of isopropanol were stirred at 60° C. and were reacted for 2 hours. After 4 g of tetracycline was added, the reaction mixture was kept at 40° to 45° C., and was reacted for 3 hours. The reaction product was filtrated and was washed with isopropanol and ethyl ether to obtain a pale yellow solid matter (compound 11) having a melting point of 154° C. (dec.). The yield was 68.6%.

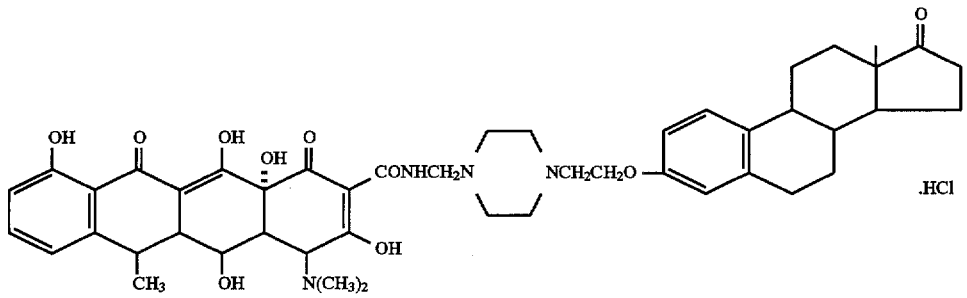

Synthesis Example 10

Synthesis of N-4-[17-oxy-estra-1,3,5 (10)-trien-3-oxyethyl]-piperazine-1-methylene-oxytetracycline (Compound 10):

0.91 g of the compound (1-2), 80 mg of polyformaldehyde and 50 ml of isopropanol were stirred and reacted at 60° C. for 2 hours. After 1.0 g of Terramycin was added, the reaction mixture was kept at 60° C. and was stirred for 3 hours. The reaction product was filtrated, was washed with isopropanol and ethyl ether and was dried to obtain a pale yellow solid matter (compound 10) having a melting point of 175° C. (dec.). The yield was 89%.

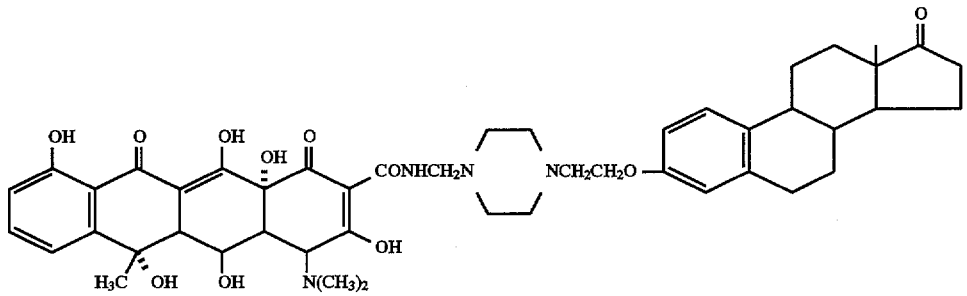

Synthesis Example 11

Synthesis of N-4-[17-hydroxy-estra-1,3,5 (10)-trien-3-ethoxyethyl]-piperazine-1-methylene-tetracycline (Compound 11):

4.1 g of N-(17-hydroxyestron-1,3,5 (10)-trien-3-oxyethyl)piperazine, 0.5 g of polyformaldehyde and 50 ml

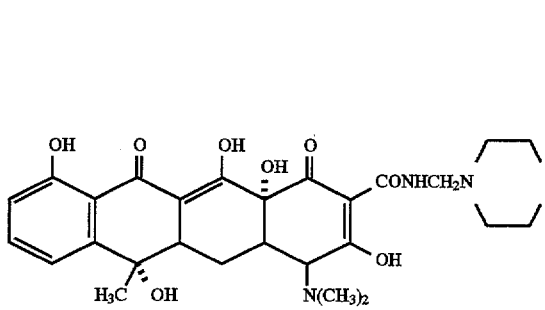

Synthesis Example 12

Synthesis of 17-hydroxy-androst-4-en-3-oxyethylaminomethylene-tetracycline:

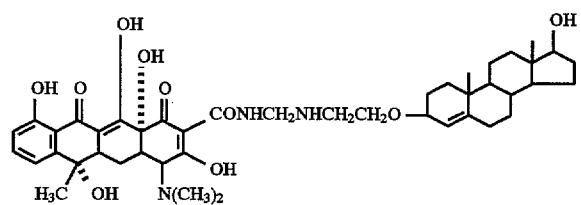

3.3 g of 3-aminoethoxy-17-hydroxy-androst-4-en, 0.3 g of metaformaldehyde and 40 ml of isopropanol were reacted at 60° C. for 4 hours. After 4.5 g of tetracycline was added, the reaction mixture was stirred and reacted for 5 hours. The reaction product was filtrated and was washed with isopropanol and ethyl ether to obtain a yellow solid matter. The yield was 92%, and the elementary analysis was as follows:

C 66.78, H 7.41, N 5.38.

Synthesis Example 13

Synthesis of 17-hydroxy-androst-4-en-3-on-6-methyleneoxyethylaminomethylene-tetracline:

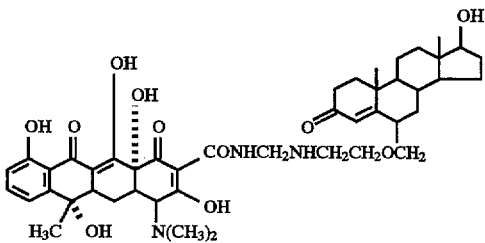

3.6 g of 6-aminoethoxymethylene-17-hydroxy-androst-4-en-3-on, 0.3 g of metaformaldehyde, 4.5 g of tetracycline and 30 ml of acetone were stirred at normal temperature for 24 hours while cutting off light, and were reacted. After the reaction was completed, the reaction product was filtrated and was washed with acetone and ethyl ether to obtain a yellow solid matter. The yield was 86%, and the elementary analysis was as follows:

C 67.90, H 7.67, N 5.18.

Synthesis Example 14

Synthesis of 17-hydroxy-androstan-3-oxyethylaminomethylene-tetracycline:

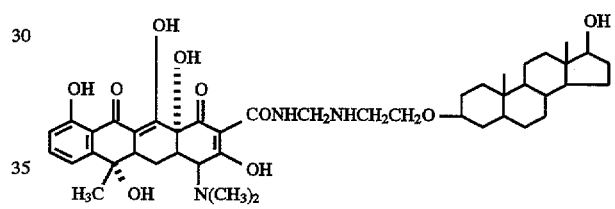

3.35 g of 3-aminoethoxy-17-hydroxy-androstan, 0.3 g of metaformaldehyde, 4.5 g of tetracycline and 30 ml of acetone were stirred and reacted at normal temperature for 30 hours while cutting off light. After the reaction was completed, the reaction product was filtrated and was washed with acetone and ethyl ether to obtain a yellow solid matter. The yield was 85%, and the elementary analysis was as follows:

C 66.61, H 7.68, N 5.40.

Synthesis Example 15

Synthesis of 17β-hydroxy-18-methyl-19-norandrost-4-en-3-on-17α-butynyleneaminomethylene-tetracycline:

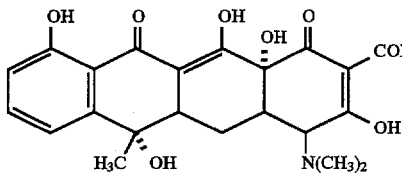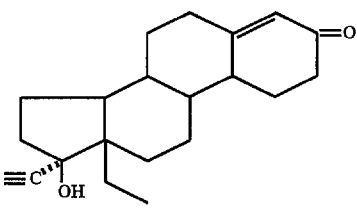

3.7 g of 17α-aminoethylethynyl-17β-hydroxy-18-methyl-19-norandrost-4-en-3-on, 0.3 g of metaformaldehyde and 30 ml of isopropanol were reacted at 60° C. for 4 hours. After 4.5 g of tetracycline was added, the reaction mixture was stirred and reacted for 6 hours. After the reaction was completed, the reaction product was filtrated and was washed with isopropanol and ethyl ether to obtain a yellow solid matter. The yield was 85% and the elementary analysis was as follows:

C 68.51, H 7.11, N 5.17.

Synthesis Example 16

Synthesis of 16α, 17β-dihydroxy-estra-1,3,5 (10)-trien-3-oxyethylaminomethylene-tetracycline:

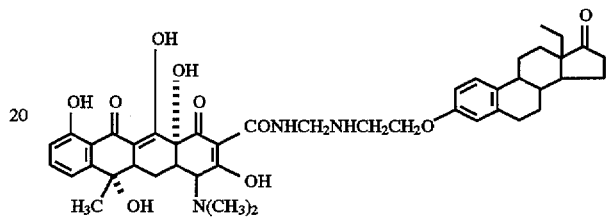

3.3 g of 3-aminoethoxy-18-methyl-estra-1,3,5 (10)-trien-17-on, 0.3 g of metaformaldehyde and 50 ml of acetone were reacted at 30° C. for 48 hours while cutting off light. After the reaction was completed, the reaction product was fil-

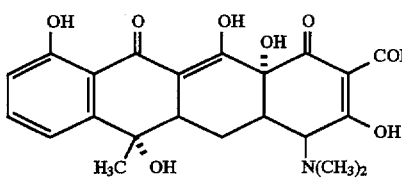

3.3 g of 3-aminoethoxy-16α, 17β-dihydroxy-estra-1,3,5 (10)-trien, 0.3 g of metaformaldehyde and 50 ml of isopropanol were reacted at 80° C. for 2 hours, and were then cooled to 40° C. After 4.5 g of tetracycline was added, the reaction mixture was reacted for 6 hours. After the reaction was completed, the reaction product was filtrated and was washed with isopropanol and ethyl ether to obtain a yellow solid matter. The yield was 85% and the elementary analysis was as follows:

C 65.48, H 6.82, N 5.13.

Synthesis Example 17

Synthesis of 18-methyl-17-oxy-estra-1,3,5 (10)-trien-3-oxyethylaminomethylene-tetracycline:

trated and was washed with isopropanol and ethyl ether to obtain a yellow solid matter. The yield was 82% and the elementary analysis was as follows:

C 67.45, H 6.86, N 5.27.

Synthesis Example 18

Synthesis of 17α-hydroxy-pregna-4-en-20-on-3-oxyethylaminomethylene-tetracycline:

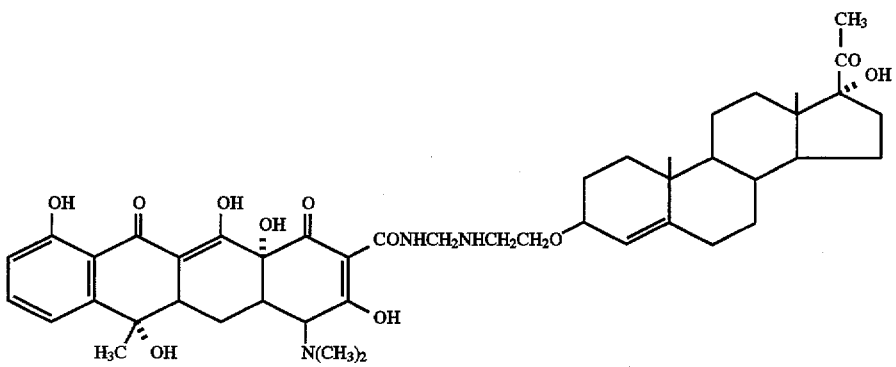

3.8 g of 3-aminoethoxy-17α-hydroxy-pregna-4-en-20-on, 0.3 g of metaformaldehyde and 50 ml of isopropanol were heated to 60° C. and reacted for 2 hours. The reaction mixture was cooled to 40° C., and 4.5 g of tetracycline was added. The reaction mixture was reacted at 60° C. for 5 hours. After the reaction was completed, the reaction product was filtrated and was washed with acetone and ethyl ether to obtain a yellow solid matter. The yield was 87% and the elementary analysis was as follows:

C 66.52, H 7.37, N 5.01.

Synthesis Example 19

Synthesis of pregna-5-en-20-on-3-oxyethylaminomethylene-tetracycline:

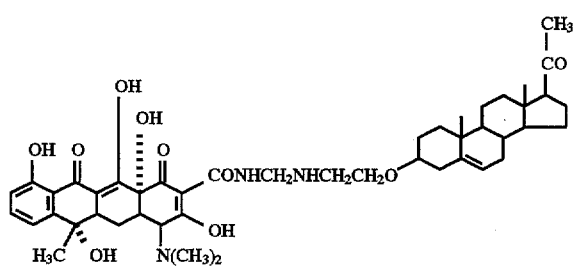

3.6 g of 3-aminoethoxy-pregna-5-en-20-on, 0.6 g of metaformaldehyde and 40 ml of isopropanol were heated to 80° C. and reacted for 2 hours. The reaction mixture was cooled to 40° C. and 4.5 g of tetracycline was added. The reaction mixture was then reacted at 40° C. for 6 hours. After the reaction was completed, the reaction product was filtrated and was washed with isopropanol and ethyl ether to obtain a solid matter. The yield was 93% and the elementary analysis was as follows:

C 67.70, H 7.36, N 5.05.

Synthesis Example 20

17-hydroxy-androst-1,4-dien-3-oxyethylaminomethylene-doxycycline:

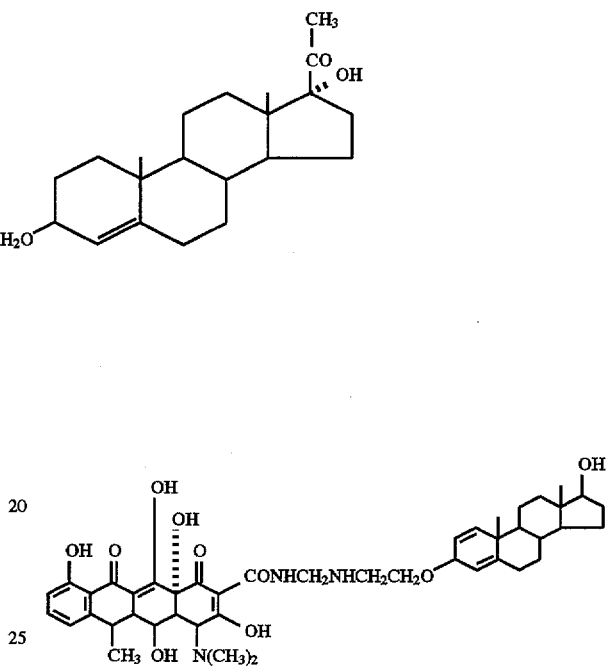

3.3 g of 3-amino-ethoxy-17β-hydroxyandrost-1,4-dien, 0.3 g of metaformaldehyde and 50 ml of isopropanol were reacted at 80° C. for 2 hours. The reaction mixture was cooled to 40° C. and then 4.5 g of doxycycline hydrochloride was added. The reaction mixture was reacted for 4 hours. After the reaction was completed, the reaction product was washed with isopropanol and ethyl ether to obtain a yellow solid matter. The yield was 89% and the elementary analysis was as follows:

C 67.23, H 7.25, N 5.28.

Synthesis Example 21

Synthesis of 17α-methyl-17β-hydroxy-androst-4-en-3-on-6-methyleneoxyethylaminomethylene-doxycycline:

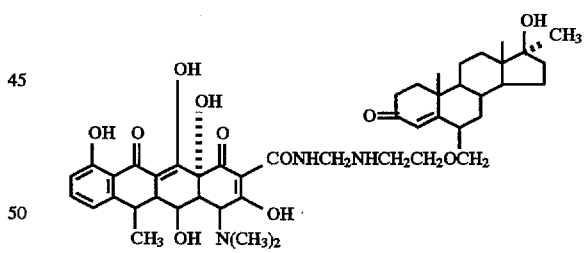

3.8 g of 6-amino-ethoxymethylene-17α-methyl-17β-hydroxy-androst-4-en-3-on, 0.3 g of metaformaldehyde and 25 ml of isopropanol were reacted at 60° C. for 4 hours. After the reaction mixture was heated and reacted, it was cooled to 40° C. and 4.5 g of doxycycline hydrochloride was added, and the reaction mixture was reacted for 8 hours. After the reaction was completed, the reaction product was washed with isopropanol and ethyl ether to obtain a yellow solid matter. The yield was 86% and the elementary analysis was as follows:

C 63.62, H 7.02, N 5.13.

Synthesis Example 22

Synthesis of 17α-methyl-17β-hydroxy-androstan-3-on-2oxyethylaminomethylene-doxycycline:

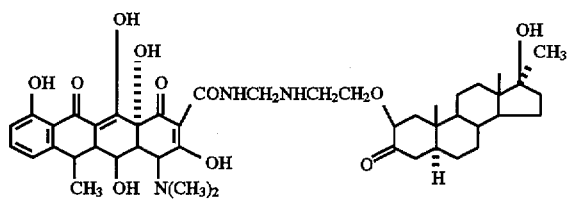

3.6 g of 2-aminoethoxy-17α-methyl-17β-hydroxy-androstan-3-on, 0.3 g of metaformaldehyde and 30 ml of isopropanol were reacted at 60° C. for 2 hours, and then 4.5 g of doxycycline hydrochloride was added. The reaction mixture was further reacted. After the reaction was completed, the reaction product was washed with isopropanol and ethyl ether to obtain a yellow solid matter. The yield was 91% and the elementary analysis was as follows:

C 65.91, H 7.51, N 5.07.

Synthesis Example 23

Synthesis of 17α-methyl-17β-hydroxy-19-norandrost-4-en-3-on-6-methyleneoxyethylamino-doxycycline:

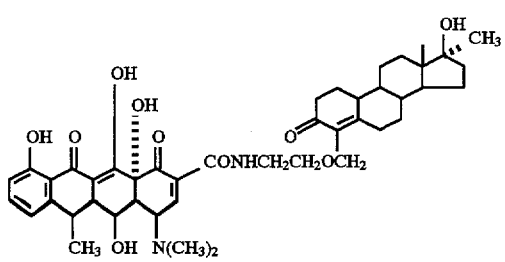

3.7 g of 6-aminoethoxymethylene-17α-methyl-17β-hydroxy-19-nor-androst-4-en-3-on, 0.3 g of metaformaldehyde and 50 ml of acetone were reacted at 30° C. for 2 hours, and 4.5 g of doxycycline hydrochloride was added. The reaction mixture was further reacted for 30 hours. After the reaction was completed, the reaction product was filtrated and was washed with isopropanol and ethyl ether to obtain a yellow solid matter. The yield was 87% and the elementary analysis was as follows:

C 63.64, H 7.03, N 5.18.

Synthesis Example 24

Synthesis of 17α-ethynyl-17β-hydroxy-androst-5-(10)-en-3-on-6-methyleneoxyethylaminomethylene-doxycycline:

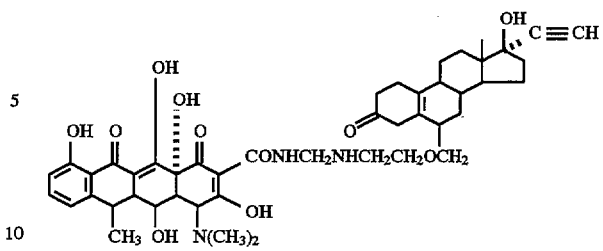

3.7 g of 6-amino-ethoxymethylene-17α-ethynyl-17β-hydroxy-androst-5-(10)-en-3-on, 0.3 g of metaformaldehyde and 50 ml of isopropanol were reacted at 60° C. for 2 hours, and 4.5 g of doxycycline hydrochloride was added. The reaction mixture was reacted at 40° C. for 8 hours. After the reaction was completed, the reaction product was filtrated and was washed with isopropanol and ethyl ether to obtain a yellow solid matter. The yield was 87% and the elementary analysis was as follows:

C 66.81, H 7.06, N 5.01.

Synthesis Example 25

17α-propylene-17β-hydroxy-11-dimethylaminophenyl-androst-4,9-dien-3-on-6-methylene-oxyethylaminomethylene-doxycycline:

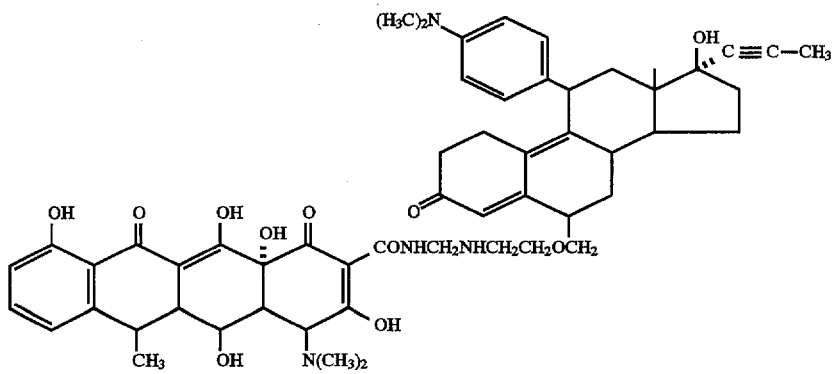

5 g of 6-amino-ethoxymethylene-11-(4'-dimethylaminophenyl)-17α-propylene-17β-hydroxy-androst-4,9-dien-3-on, 0.3 g of metaformaldehyde and 40 ml of isopropanol were heated and reacted at 80° C. for 2 hours. After the reaction mixture was cooled to 40° C., 4.5 g of doxycycline hydrochloride was added and reaction mixture was reacted for 6 hours. After the reaction was completed, the reaction product was filtrated and was washed with isopropanol and ethyl ether to obtain a yellow solid matter. The yield was 90% and the elementary analysis was as follows:

C 68.76, H 6.88, N 5.72.

Synthesis Example 26

Synthesis of 16,17-isopropylidene-16,17-dioxyestra-1,3,5 (10)-trien-3-oxyethylaminomethylene-doxycycline:

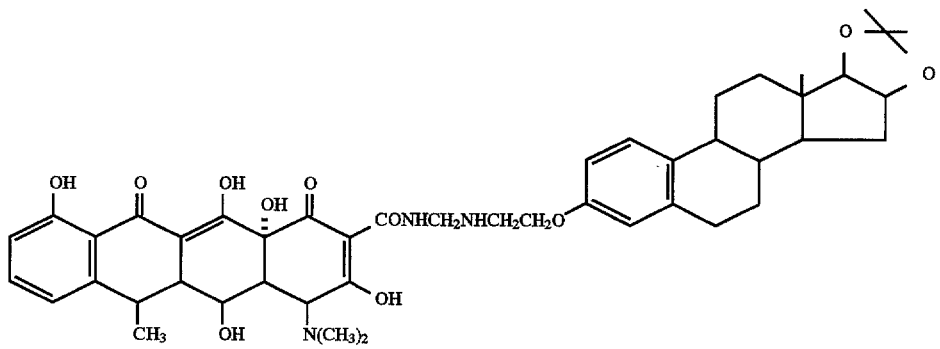

3.7 g of 16,17-isopropylidene-16,17-dioxy-estra-1,3,5 (10)-trien-3-aminoethyl ether, 0.3 g of metaformaldehyde and 50 ml of isopropanol were reacted at 60° C. for 2 hours, and 4.5 g of doxycycline hydrochloride was added. The reaction mixture was further reacted for 8 hours. After the reaction was completed, the reaction product was filtrated and was washed with isopropanol and ethyl ether to obtain a yellow solid matter. The yield was 95% and the elementary analysis was as follows:

C 66.61, H 6.90, N 5.18.

Synthesis Example 27

Synthesis of 3,17-dihydroxy-estra-1,3,5 (10)-trien-17-acetate-7-methyleneoxyethylaminomethylene-doxycycline:

3.8 g of 7-aminoethyloxymethylene-estra-3,17-dien-17-acetate, 0.3 g of metaformaldehyde and 50 ml of isopropanol were reacted at 60° C. for 4 hours, and 4.5 g of doxycycline hydrochloride was added. The reaction mixture was further reacted for 4 hours. After the reaction was completed, the reaction product was filtrated and was washed with isopropanol and ethyl ether to obtain a yellow solid matter. The yield was 88% and the elementary analysis was as follows:

C 65.34, H 6.68, N 4.95.

Synthesis Example 28

Synthesis of 17-hydroxy-pregna-4-en-20-on-3-oxyethylaminomethylene-doxycycline:

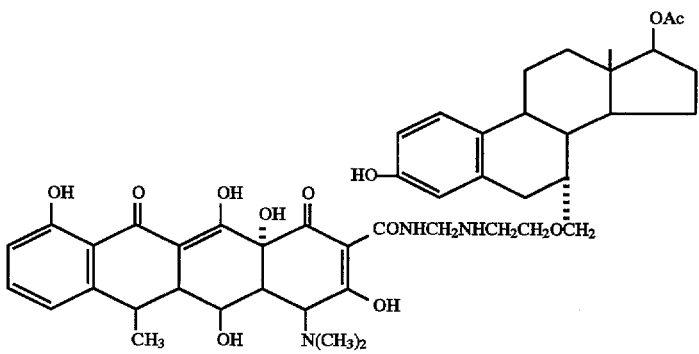

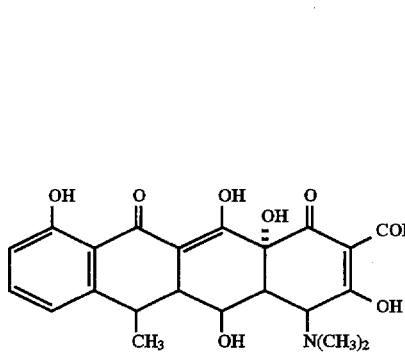

3.7 g of 3-aminoethyoxy-17α-hydroxypregna-4-en-20-on, 0.3 g of metaformaldehyde and 40 ml of isopropanol were heated and reacted at 60° C. for 2 hours, and 4.5 g of doxycycline hydrochloride was added. The reaction mixture was further reacted for 4 hours. After the reaction was completed, the reaction product was filtrated and was washed with isopropanol and ethyl ether to obtain a yellow solid matter. The yield was 92% and the elementary analysis was as follows:

C 66.41, H 7.40, N5.14.

Synthesis Example 29

Synthesis of pregna-4-en-3,20-dion-6-methylene-oxyethylaminomethylene-doxycycline:

hydrochloride was added. The reaction mixture was further reacted for 4 hours. After the reaction was completed, the reaction mixture was further reacted for 4 hours. After the reaction was completed, the reaction product was filtrated and was washed with isopropanol and ethyl ether to obtain a yellow solid matter. The yield was 93% and the elementary analysis was as follows:

C 67.77, H 7.36, N 4.59.

Synthesis Example 30

Synthesis of 3,17-dihydroxy-estra-1,3,5 (10)-trien-11-(4-phenoxy-ethylamino)-methylene-doxycycline:

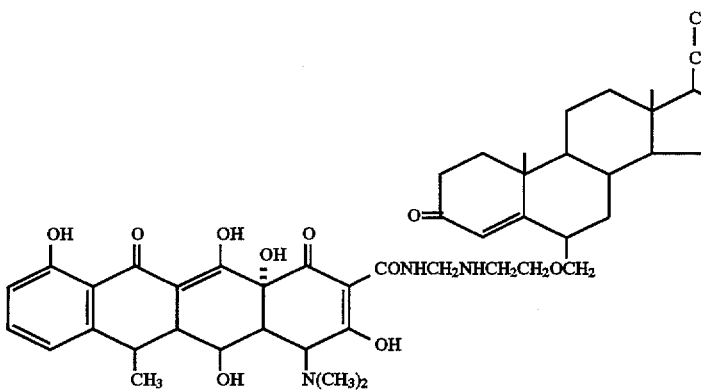

3.9 g of 6-aminoethoxymethylene-pregna-4-en-3,20-dion, 0.3 g of metaformaldehyde and 50 ml of isopropanol were reacted at 60° C. for 3 hours and 4.5 g of doxycycline

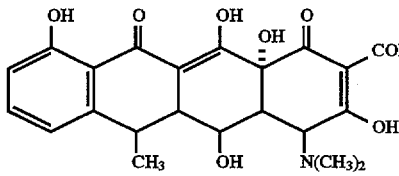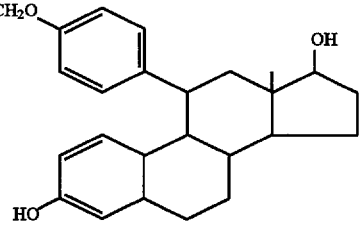

4 g of 11-(4'-aminoethoxyphenyl)-3,17-dihydroxy-estra-1,3,5 (10)-trien, 0.3 g of metaformaldehyde and 50 ml of isopropanol were reacted at 60° C. for 2 hours and 4.5 g of doxycycline hydrochloride was added. The reaction mixture was further reacted for 8 hours. After the reaction was completed, the reaction product was filtrated and was washed with isopropanol and ethyl ether to obtain a yellow solid matter. The yield was 89% and the elementary analysis was as follows:

C 68.13, H 6.69, N 4.73.

Synthesis Example 31

Synthesis of 17β-hydroxy-17α-methyl-andrstano-(3,2-C)-pyrazol-N-methylene-tetracycline:

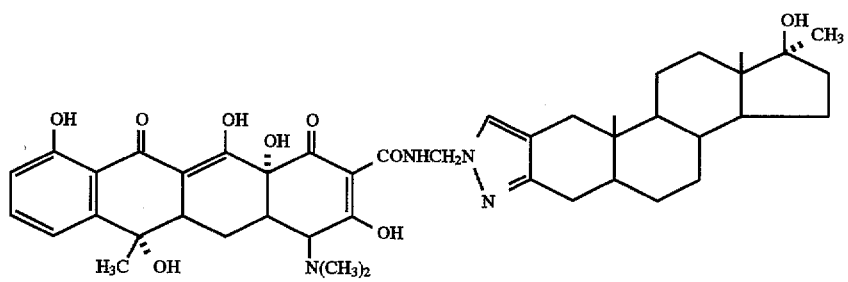

3.29 g of 17β-hydroxy-17α-methyl-androstano-(3,2-C)-pyrazol, 0.3 g of metaformaldehyde and 30 ml of isopropanol were reacted at 40° C. for 2 hours and 4.5 g of tetracycline. The reaction mixture was stirred and reacted for 6 hours. After the reaction was completed, the reaction product was filtrated and was washed with isopropanol and ethyl ether to obtain a yellow solid matter. The yield was 89% and the elementary analysis was as follows:

C 67.48, H 7.07, N 7.30.

drop of n-octyl alcohol were put into the test tube, and the test tube was left in a water bath at 75° C. for 45 minutes. Next, 0.1 ml of this digestive fluid was sampled and was placed into a bottle storing a scintillating solution and furthermore, 5 ml of 0.5% scintillating solution was mixed. After the solution became transparent, it was placed into an FJ2105 liquid scintillation counter so as to measure radioactivity and to determine cpm of the sample. Separately, dpm of 52 samples obtained from four groups of animals was measured (External Standard Method).

The quantity of the drug in the tissue was determined in the following way.

Drug quantity in tissue (cpm/mg)=(sample cpm)÷(digested tissue quantity (mg))

Drug quantity in tissue (μg/mg)=(sample cpm/mg×6)÷(count efficiency (E)×2.22×$10^7$×0.34 mCi/mg (specific radioactivity))

The results were as follows.

Experiment 1

Intracorporeal Distribution of Compound

The compound 1-3 produced in Synthesis Example 1-3 was subjected to radioactive labelling by $^3$H (0.34 mCi/mg), and was injected into the vein of the tail of mice in a dosage of 20 μCi/20 g. Groups of mice each comprising five mice were killed at 1 minute, 5 minutes, 15 minutes, 30 minutes, 1 hour, 4 hours, 6 hours, 24 hours, 48 hours and 72 hours after the injection, and 50 μl of the blood was collected from the eye socket of each mouse. Further, the heart, the ovary, the womb, the small intestine, bones (thighbone), etc., were collected from each mouse, and 50 mg of the tissue (50 μl for the blood) was placed into a plastic test tube. Further, 0.2 ml of perchloric acid, 0.4 ml of hydrogen peroxide and a

TABLE 1

Change of drug concentration in blood (mean value of 5 animals at each time)
Change of drug concentration in blood (cpm/50 μl) after intravenous injection of $^3$H- compound 1-3.

| time after injection | 1 min. | 5 min. | 15 min. | 30 min. | 1 hr. | 4 hr. | 6 hr. | 24 hr. | 48 hr. | 72 hr. |
|---|---|---|---|---|---|---|---|---|---|---|
| cpm | 8665 | 5238 | 2638 | 2347 | 952 | 659 | 715 | 523 | 272 | 190 |
| SD | ±1700 | ±2263 | ±941 | ±452 | ±88 | ±60 | ±57 | ±102 | ±40 | ±25 |

TABLE 2

Change of drug quantity in tissue (cpm/mg tissue)

| hour | heart | ovary | womb | muscle | brain | stomach | intestines | bone |
|---|---|---|---|---|---|---|---|---|
| 1' | 40 | 40 | 28 | 28 | 20 | 30 | 53 | 38 |
| 5' | 43 | 48 | 37 | 32 | 13 | 39 | 138 | 32 |
| 15' | 38 | 37 | 24 | 15 | 9 | 28 | 85 | 23 |
| 30' | 37 | 41 | 30 | 22 | 10 | 32 | 150 | 23 |
| 1° | 13 | 19 | 12 | 11 | 7 | 12 | 28 | 15 |
| 4° | 8 | 15 | 7 | 7 | 7 | 10 | 13 | 11 |
| 6° | 10 | 17 | 9 | 6 | 6 | 9 | 12 | 9 |

TABLE 2-continued

Change of drug quantity in tissue
(cpm/mg tissue)

| hour | heart | ovary | womb | muscle | brain | stomach | intestines | bone |
|---|---|---|---|---|---|---|---|---|
| 24° | 8 | 7 | 4 | 4 | 4 | 6 | 6 | 9 |
| 48° | 4 | 7 | 4 | 5 | 4 | 4 | 4 | 6 |
| 72° | 4 | 6 | 4 | 4 | 3 | 3 | 3 | 5 |

*Mean value of five animals

TABLE 3

Change of drug quantity in tissue
(μg/mg tissue)

| hour | heart | ovary | womb | intestines | bone |
|---|---|---|---|---|---|
| 1' | 0.834 | 0.822 | 0.588 | 1.104 | 0.780 |
| 5' | 0.894 | 0.99 | 0.774 | 2.874 | 0.654 |
| 15' | 0.792 | 0.762 | 0.204 | 1.770 | 0.468 |
| 30' | 0.270 | 0.846 | 0.624 | 3.126 | 0.468 |
| 1° | 0.270 | 0.390 | 0.252 | 0.582 | 0.306 |
| 4° | 0.168 | 0.306 | 0.144 | 0.270 | 0.228 |
| 6° | 0.210 | 0.348 | 0.186 | 0.252 | 0.186 |
| 24° | 0.168 | 0.150 | 0.084 | 0.126 | 0.186 |
| 48° | 0.084 | 0.150 | 0.084 | 0.084 | 0.126 |
| 72° | 0.084 | 0.126 | 0.084 | 0.066 | 0.102 |

*Mean value of five animals

Experiment 2

Acute Toxicity Test (1) Sample:

The compound 1-3 was pale yellow crystalline powder and its lot number was 930113. The solution was a pale yellow transparent solution, and has a concentration of 50 mg/ml and a pH of about 5. It was offered by the Osteoporosis Research Laboratory, School of Pharmacy, West China University of Medical Sciences (WCUMS).

(2) Animals:

Kunming species mice, health: first class, weight: 18 to 21 g, half male and half female. The mice were offered by the Experimental Animal Center of WCUMS.

(3) Measurement of half lethal dose ($LD_{50}$):

Four to five dose groups were prepared in equal ratios (1:0.7 to 0.8) within the LD range of 0 to 100% obtained by preliminary tests. The drug for peroral administration was prepared by suspending the solid compound 1-3 in 1% $CMCNa_2$ to form a suspension. For injection, drug solutions having different concentrations were prepared by dissolving the compound 1-3 in physiological saline solution by a low specific gravity dilution method. The animals were starved (but without limiting water), and 20 hours later, ten mice were grouped at random into each group irrespective of their sex and body weight. The drug was dosed once a day in a dose of 0.2 ml/10 g and the animals were inspected. Dead animals were dissected and any change of the morbid state was examined with by the naked eye.

(4) Test Results:

(a) Measurement of maximum tolerance dose of compound 1-3 to mice:

Maximum tolerance dose when no death was observed at the time of preliminary tests was measured. After the test compounds were dosed once in the maximum concentration and in the maximum capacity for peroral administration to 20 mice (10 males and 10 females), the animals were examined for 7 days. As a result, no abnormality was found in the mice and no mouse was dead, either. The maximum tolerance dose (MTD) was >6 g/kg.

(b) The results after the compound 1-3 was injected to the vein of the tail of the mice were as follows.

TABLE 4

| Test sample dosage (mg/kg) | logarithmic dosage (X) | No. of animals | No. of dead animals | death ratio (%) | provit unit (Y) |
|---|---|---|---|---|---|
| 250 | 2.3979 | 10 | 10 | 100 | |
| 200 | 2.3010 | 10 | 10 | 100 | 7.40 |
| 160 | 2.2041 | 10 | 8 | 80 | 5.84 |
| 128 | 2.1072 | 10 | 2 | 20 | 4.16 |
| 102.4 | 2.0103 | 10 | 0 | 0 | 2.60 |

Calculation processing: by Bliss method $LD_{50}$=143.11 mg/kg $LDg_{50}$: inside range of 95% reliability limit: 132.95 to 154.05 mg/kg (5) Conclusion:

The maximum tolerance dose (MTD) of compound 1-3 for single administration to the mice was at least 6 g/kg and its toxicity was extremely low. The $LD_{50}$ for the intravenous injection to the vein of the tail of the mice was 143.11 mg/kg. After intravenous injection, activity of the mice decreased and then the mice started jumping and went into spasm. The eyeball protruded and changed to white, and incontinence of urine and feces was observed. Although the major proportion of the poisoned animals died instantly, the very few that survived were also dead within 24 hours. Those survived for more than 24 hours were not dead within 7 days. No difference was found between the sexes of the dead animals, and any change of the morbid state could not at all be observed by the naked eye in the dissection of the dead animals. The room temperature of the testing room was 17° C.

Experiment 3: Osteogenesis Test (1)

A first generation incubation system of the osteoblast originating from the caivaria of Whister rats (female, 6-months' age) was used as the test cells. After the start of incubation, the test compounds (compound 1-3) were added once a day to the medium in a dose of $10^{-6}$M, $10^{-8}$M or $10^{-9}$M on the second and third days (propagation period). Alternatively, the compound 1-3 in the amount described above was added once a day to the medium for 4 days (calcification period) from the seventh day from the start of incubation. On the fourteenth day from the start of incubation, the cells were subjected to von Kossa dyeing and detection of phosphates was carried out. The area of the bone knots which were dyed to brown was confirmed by the naked eye and was used as the index for osteogenesis. The results were as follows.

TABLE 5

Osteogenesis promotion function of compound 1-3

| addition concentration (M) | propagation period | calcification period |
|---|---|---|
| $10^{-9}$ | → | ↑ |
| $10^{-8}$ | → | ↑↑ |
| $10^{-6}$ | → | ↑ |

TABLE 5-continued

Osteogenesis promotion function of compound 1-3

| addition concentration (M) | propagation period | calcification period |
|---|---|---|

*Transverse arrow indicates that osteogenesis did not exist and upward arrow indicates promotion of osteogenesis FIGS. 1 to 3 show the results when the same procedure described above was repeated three times. In the drawings, symbol A represents no addition of the drug, B represents addition in $10^{-9}$M, C represents addition in $10^{-8}$M and D represents addition in $10^{-6}$M.

As is obvious from the results described above, the compound of the present invention exhibited the osteogenesis promotion function.

Experiment 4: Osteogenesis Experiment 2

A first generation incubation system of the marrow cells originating from the thighbones of Whister rats (female, 6-months' age) were used as the cells for the experiments, and the compound 1-3 were added once a day in an amount of $10^{-8}$M or $10^{-6}$M to the medium on the seventh, ninth and eleventh days from the start of incubation (calcification period). Evaluation was carried out in the same way as in Experiment 3. The results were tabulated in the following table.

TABLE 6

Osteogenesis promotion function of Compound 1-3

| addition quantity (M) | Osteogenesis promotion |
|---|---|
| $10^{-8}$ | ↑ |
| $10^{-6}$ | → |

As is obvious from the table given above, the compound of the present invention exhibited the osteogenesis promotion function.

Experiment 5: Pharmacological Study of Anti-osteoporotic Effect of Compound 1-3

I. Experiment Design:

Clinical observations in an experiment on the pharmacological effect of compound 1-3 against osteoporosis in castrated rats clearly showed the possibility that bone loss due to estrogen deficiency in postmenopausal women may provoke osteoporosis. A relatively satisfactory therapeutic effect is obtained by estrogen therapy, but its long-term use carries the risk of inducing endometrial cancer, breast cancer, etc. and consequently its clinical application is restricted. In order to overcome the disadvantages and enhance the therapeutic effect, School of Pharmacy, West China University of Medical Sciences, has improved the structure of estrogen and synthesized the anti-osteoporotic compound 1-3. Upon completion of toxicity testing, castrated osteoporotic rat models and cultured UMR106 osteoblasts were used, and the effect of the drug on the osteoporosis models and cells was observed to determine the therapeutic effect and efficacy of compound 1-3 against osteoporosis and establish a basis for clinical application of the drug.

II. Materials and Methods (i) Drugs:

Compound 1-3 (synthesized at School of Pharmacy West China University of Medical Sciences). 0.1N HCl was used to prepare a 10 mg/ml stock solution, and the experimental concentrations were diluted with distilled water.

To 100 mg of estradiol (West China University of Medical Sciences (WCUMS)) were added 5 ml of 90% alcohol and 20 ml of polyethylene glycol 400, and the mixture was placed in water and heated to 90° C. for dissolution. It was then diluted to 100 ml with distilled water to prepare a 1 mg/ml stock solution.

Calcium preparation (both calcium carbonate and citric acid produced at Peking Chemical Factory). 100 mM of citric acid was added to 100 mM of calcium carbonate (2.1 g of citric acid was added to 1 g of calcium carbonate, and placed in 100 ml of distilled water. Prepared prior to use). Labelled with $^3$H-TdR (Chinese Academy of Sciences, Radiation Laboratory).

All other reagents and drugs were AR grade (Peking Chemical Reagents Co.)

(ii) Animals:

Wistar rats, 80 female, 20 male, 5–6 months old, body weight 260±10 g (China University of Medical Sciences, Animal Laboratory); the body weights of all animals were measured and recorded prior to the start of the experiment.

(iii) Grouping of animals for experiment

1. The healthy female Wistar rats were divided into 10 groups with 6 rats per group, which were assigned numbers as listed below.

The 10 groups were as follows:

(1) 7-stage surgery group
(2) Control surgery group
(3) Low dosage (compound 1-3, 50 µg/rat/day)
(4) Medium dosage (compound 1-3, 500 µg/rat/day)
(5) High dosage (compound 1-3, 5 mg/rat/day)
(6) Compound 1-3, 500 µg/rat+0.5 ml Ca
(7) Estradiol, 0.5 mg/rat/day
(8) Estradiol, 0.5 mg/rat/day+0.5 ml Ca
(9) Compound 1-3, 500 µg/rat/day+0.5 ml Ca (administered at 5th week after surgery)
(10) Compound 1-3, 500 µg (5th week after surgery), intraperitoneal administration Groups 1-8 were given oral administration for 1 week after surgery. Group 9 was given oral administration for 5 weeks after surgery. Group 10 was given intraperitoneal administration from the 5th week after surgery.

2. The healthy male Wistar rats were separated into 3 groups assigned as group 11 (Sham-operated), group 12 as an orchiectomized control, and group 13 which was given 500 µg/rat/day of compound 1-3 for 1 week after orchiectomy.

3. The animals in each group were administered 6 times a week, with the control group receiving distilled water, and at the 13th week all the animals were killed by decapitation, and blood and tissue samples were taken simultaneously.

(iv) Preparation of animal models

The experimental female Wistar rats of 5–6 weeks old with body weights of 260±10 g had been provided by the China University of Medical Sciences, Animal Laboratory. They were starved for 12 hours prior to surgery. Each of the rats was anesthetized by intraperitoneal injection of pentobarbital sodium (35 mg/kg) and fixed on their back on the surgical board, and an approximately 33 mm hole was opened at the center of the hypogastrium to expose the pink Y-shaped uterus. The dark red cystic globes at the top of the uterus are the ovaries. The bottom section was ligated with silk thread, and both ovaries were cut out with surgical scissors. After confirming lack of bleeding, the muscle and skin were sutured, returning the uterus to its original position. In Sham-operated group, the uteri were simply exposed without being cut out. After surgery, penicillin was injected into the abdomen (80,000 units/rat) to prevent infection. After a few hours, the rats returned to a normal state.

The testicles were removed from the experimental male Wistar rats using the same anesthetic method, with Sham group having only a section of the skin of the testicles opened and then sutured, without removal. The local area was disinfected.

(v) Observed indicators:
1. Body weight: Measured once a week
2. Vaginal smear of female rats was observed continuously for 6 days at the 10th week (proestrum, estrum, interval).
3. Urine was collected for 24 hours (12th week) and the urine Ca, P and creatine were measured.
4. The bone density of each rat was measured at the 13th week just before decapitation.
5. The animals were decapitated at the 13th week, and the following parameters were observed.
   (1) Blood serum was taken, and the Ca, P and alkaline phosphatase contents were measured.
   (2) The uteri were taken and their weights were measured.
   (3) The livers and kidneys were taken and each of them were observed for drug toxicity and drug reception.
   (4) The bone stress of the right thigh bone was measured.
   (5) 20% decalcified nitrate was added to the left thigh bone and observed for morphological changes.
   (6) The right shank bone was incinerated, and the bone ash was weighed and measured for Ca and P.
   (7) A receptor test was conducted on the left shank bone.
(vi) Cells cultivation UMR106 cells were cultured in a DMEM/HamF-12 medium containing 10% FCS, under 37° C. and 5% $CO_2$. Digestion was performed once every 3 days with trypsin-EDTA, then succeeded.

1. $^3$H-TdR incorporation test.

The digestive cells were centrifuged at 2000 rpm×10 min, and added DMEM/HamF-12 non phenol red medium containing 7.5% CS-FCS (4 g NoritA charcoal+100 ml FCS) then 3×10$^4$/ml of cells were measured with 24-orifices of culture board (1 ml/orifice). After 24 hours medium was replaced with DMEM/HamF-12 non phenol red containing 0.2% FSA.

Test compounds (estradiol, compound 1-3) were administered after 48 hours cultivation. 0.5 µCi/orifice of $^3$H-TdR was administered for 32 hours. After 48 hours of administration, washing was performed 5–6 times with PBS solution, 0.2N NaOH was added at 1 ml/orifice, and after 24 hours a toluene-triton scintillation solution was used for emission and the value was measured.

2. Measurement of cell number

At 48 hours after the administration to the cells in the 24-orifice culture board, cells were digested with trypsin-EDTA and counted.

3. The activity of ATP secreted from cells was measured.

At 48 hours after the administration to the cells on the 24-orifice culture board, the medium was pipetted out and the ATP was measured by biochemical colorimetry.

III. Results (i) The change of cells from vaginal smear was observed.
1. Standards for judgment At the 10th week after the operation, vaginal smear was microscopically observed continuously for 6 days.

Index of estruation: Enormous volume of large indefinite keratinized epithelial cells including a small voluml of epithelial cells were observed.

Index of duration of estruation: Enormous volume of multinuclear white cells including a small volume of epithelial cells were observed.

2. Results

TABLE 7

| Classification | n = 5 Estrous days per week |
|---|---|
| Shain-operated group | 3 |
| OVX | 1–2 |
| +Compound 1-3 0.05 mg/rat/day | 5–6 |
| +Compound 1-3 0.5 mg/rat/day | 5 |
| +Compound 1-3 5 mg/rat/day | 5–6 |
| +Compound 1-3 0.5 mg/rat/day | 4–6 |
| +$E_2$ 0.5 mg/rat/day | 5–6 |
| +$E_2$ 0.5 mg/rat/day + Ca | 5–6 |
| +Compound 1-3 0.5 mg/rat/day + Ca (5 weeks after administration) | 5–6 |
| +Compound 1-3 0.5 mg/rat/day, intraperitoneal (5 weeks after administration) | 4–5 |

Conclusion: Change of estruation was seen 3 times a week in Sham-operated group. Change of estruation was seen 1–2 times for 1 week after operation, but all of the groups administered the drug after operation showed change of estruation 4–6 times in one week. This confirmed that the compound and $E_2$ influenced the change of estruation of rats.

(ii) Body weight changes

There was not much difference in body weight changes between the operated groups and Sham-operated group, but the group given $E_2$ therapy after operation clearly had a higher increase in body weight than the operated group. The body weights of the group given 0.05 mg/day of compound 1-3 and the group given 0.5 mg/day of compound 1-3 5 weeks after operation, and of the group given intraperitoneal administration 5 weeks after operation, clearly had a higher increase than the operated group. The body weight increases in the groups given 0.5 mg/day and 5 mg/day of compound 1-3 were not very different from those in the Sham-operated group.

Effect of compound 1-3 on body weight of castrated female rats (see Table 8).

TABLE 8

Effect of compound 1-3 on body weight of castrated male rats

| Group | Body weight change | | | |
|---|---|---|---|---|
| | Actual increase (g) X ± SD | Body weight (g) X ± SD | No. of animals | Times measured |
| Sham-operated group | 51 ± 5.0 | 302 ± 5.4 | 6 | 9 |
| Operated group | 57 ± 6.0 | 298 ± 6.5 | 6 | 9 |
| Compound 1-3 (oral) 5 mg/rat/day | 59 ± 5.0 | 297 ± 5.6 | 6 | 9 |
| 0.5 mg/rat/day | 47 ± 5.0 | *308 ± 5.1 | 6 | 9 |
| 0.05 mg/rat/day | *94 ± 8.0 | **312 ± 8.8 | 6 | 9 |
| Compound 1-3 0.5 mg + Ca | 54 ± 6.0 | 304 ± 6.0 | 6 | 9 |
| Compound 1-3 0.5 mg + Ca (after 5 weeks) | *73 ± 9.0 | 302 ± 9.4 | 6 | 9 |

TABLE 8-continued

Effect of compound 1-3 on body weight of castrated male rats

| | Body weight change | | | |
|---|---|---|---|---|
| Group | Actual increase (g) X ± SD | Body weight (g) X ± SD | No. of animals | Times measured |
| $E_2$ | *73 ± 8.0 | 305 ± 7.9 | 6 | 9 |
| $E_2$ + Ca | *72 ± 10.0 | **320 ± 10.3 | 6 | 9 |
| Compound 1-3 (ip) 0.5 mg/d | **86 ± 12.0 | **324 ± 12.1 | 6 | 9 |

Note: As compared with operated group, *P < 0.05 **P < 0.01

The body weights of the male rats in the group given 0.5 mg of compound 1-3 orally and the operated control group clearly showed greater increase (P<0.01) than the Sham-operated group, but there was not much difference between the weight increases of the administered group and the control group.

Figure 4:
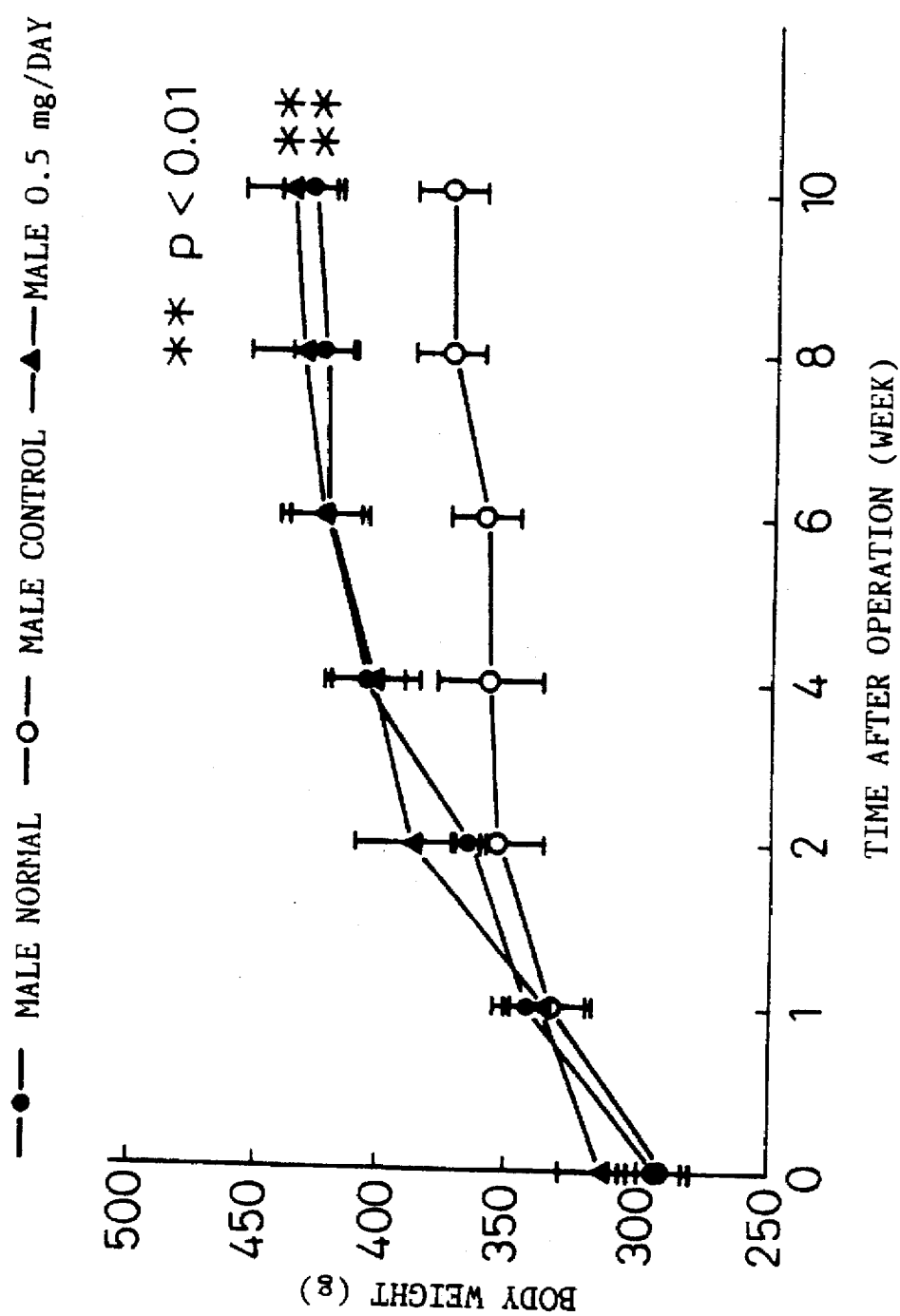
FIG. 4 is a graph showing an effect of the compound 1-3 on the body weight of castrated rats.

Effect of compound 1-3 on body weights of castrated male rats (see FIG. 4)

(iii) Changes in uterine weight:
1. Compared with Sham-operated group.

After completion of operation on the operated group, compound 1-3 was orally administered for 12 weeks in at 5 mg/d, 0.5 mg/d and 0.05 mg/d and intraperitoneally administered for 6 weeks at 0.5 mg/d, and this was supplemented with $E_2$. The uterine weights all showed clear decreases.

2. Compared with operated group.

After operation, there were slight increases in uterine weights in the groups given 5 mg/d and 0.05 mg/d of compound 1-3 orally for 12 weeks. This indicates that the test compound has an increasing effect on uterine weight after operation.

(iv) Bone density measurement: See Table 9.

Figure 5:
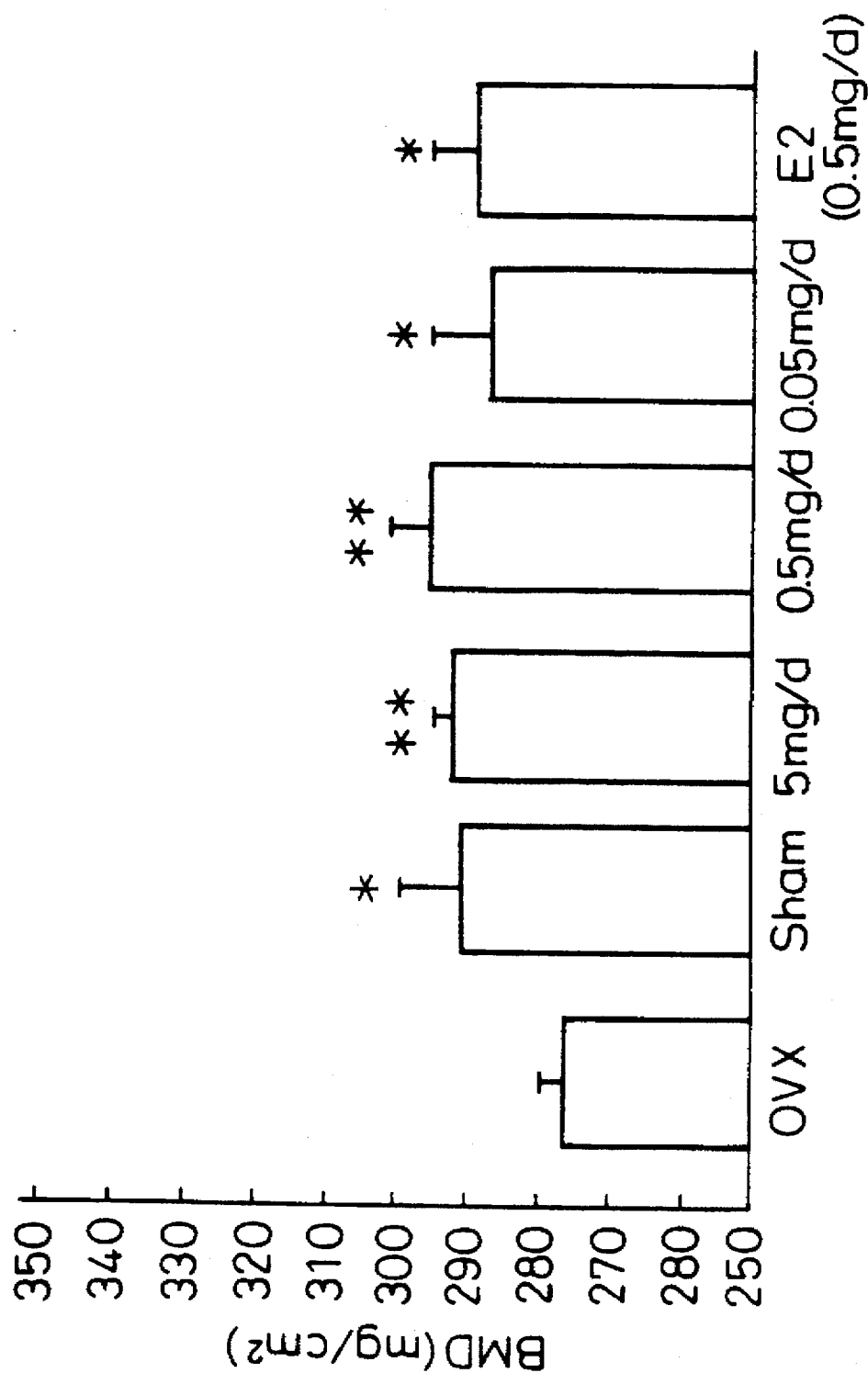
FIG. 5 is a graph showing an effect of the compound 1-3 on bone density (BMD) of castrated rats.
Figure 6:
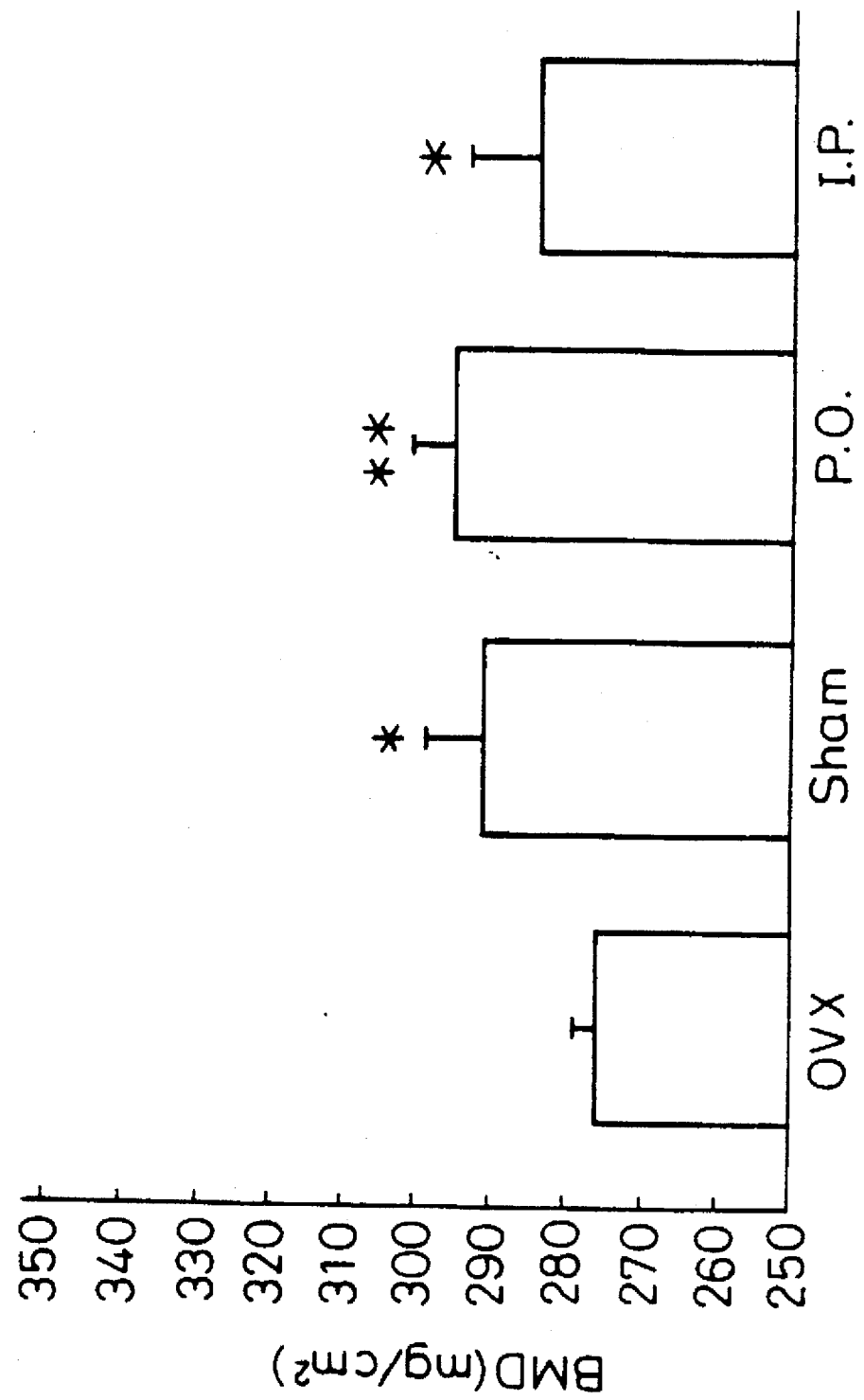
FIG. 6 is a graph showing an effect of the compound 1-3 on the bone density (BMD) of DVX rats.

1. The bone density of the operated group was clearly lower than the Sham-operated group.
2. 0.5 mg of $E_2$ was injected via the gaster, and when compared with the operated group after 12 weeks, the bone density was clearly higher, whereas there was not much difference in comparison with the Sham-operated group.
3. Compound 1-3 has a clear effect on changes in bone density after operation. A dose-dependent relationship was exhibited (see FIG. 5).
4. 0.5 mg of compound 1-3 gave a clearly higher bone density than 0.5 mg of $E_2$ (see FIG. 5).
5. When compound 1-3 was administered orally and intraperitoneally, both showed marked increases in bone density which were similar (see FIG. 6).
6. With administration for 1 week and 5 weeks after operation, both showed clear increases in bone density (see FIG. 7).

TABLE 9

Results of bone density measurement

| Group | BMD (mg/cm$^2$) X ± SD | | Comparison with surgery group |
|---|---|---|---|
| Sham-operated group | 291 ± 8 | n = 6 | P < 0.05 |
| Operated group | 276 ± 3 | n = 6 | |
| 0.05 mg compound 1-3 | 287 + 8 | n = 6 | P < 0.05 |
| 0.5 mg compound 1-3 | 295 ± 6 | n = 6 | P < 0.01 |
| 5 mg compound 1-3 | 292 ± 2 | n = 5 | P < 0.01 |
| 0.5 mg compound 1-3 + Ca$^{2+}$ | 287 ± 6 | n = 6 | P < 0.05 |
| 0.5 mg $E_2$ | 289 ± 6 | n = 6 | P < 0.01 |
| 0.5 mg $E_2$ + Ca$^{2+}$ | 287 ± 8 | n = 6 | P < 0.05 |
| 0.5 mg compound 1-3 + Ca$^{2+}$ (5 weeks after surgery) | 289 ± 10 | n = 6 | P < 0.05 |
| 0.5 mg compound 1-3 (ip, 5 weeks after surgery) | 284 ± 9 | n = 5 | P < 0.05 |

(v) Results for calcium, phosphorus

After the ovaries were removed from the rats, the blood calcium levels increased and the phosphorus levels were lowered, but there was no notable difference. Changes in the blood Ca and P levels were observed after the administration treatment.

1. Blood Ca$^{2+}$: The blood calcium levels were restored to a normal level by 5 mg/day of compound 1-3. There was a clear difference between the treated group and the operated control group, with P<0.01. There was no effect in the group given 0.05 mg/day of compound 1-3.

$E_2$ treatment: With both simple administration of $E_2$ and in combination with the calcium preparation, the blood calcium levels of OVX rats were restored. There was a clear difference between the $E_2$+Ca group and the operated control group, with P<0.01.

2. Blood P: Blood P levels were restored with both 0.5 mg/day and 5 mg/day of compound 1-3, but the restoration was even clearer with 0.05 mg/day. The treated group had a clear difference compared to the surgery control group, with P<0.01.

(vi) Serum osteocalcin (BGP) results:

After ovariectomy, the serum BGP rose slightly, and after treatment with compound 1-3 the BGP levels fell, dose dependently. The rats in the group given 5 mg/day of compound 1-3 all had clear reductions in comparison with the Sham-operated group and OVX group, with P<0.05. The group treated with 0.05 mg/day of compound 1-3 had a clearly greater reduction than the OVX control group, with P<0.05.

(vii) Changes in serum ALP

The serum ALP of the OVX rats increased slightly more than the Sham-operated group, and although the group treated with 0.5 mg/day $E_2$ had somewhat greater reduction than the operated group, there was no clear difference. Treatment with the compound raised serum ALP levels of the OVX rats dose dependently. The groups treated with 0.5 mg/day and 5 mg/day of compound 1-3 had respective differences of P<0.05 and P<0.001 in comparison with the Sham-operated group.

(viii) Changes in bone stress:

Animals were decapitated, and the thigh bones were sorted and placed in small bottles containing physiological saline which were labelled with assigned numbers. They were then tested with an electronic universal tester.

The conditions of the dynamic indicators of the thigh bones were tested.

1. Method: 3-point bending test with simple beam.
2. Direction: Front to back
3. Testing distance: 25 mm
4. Rupture strength defined as breaking weight, expressed in kg 5. Flexural strength expressed as breaking weight, with deviation in working point expressed as kg/mm.

Each group was studied by t test and analysis of variance to determine the effect of compound 1-3 on the dynamic indicators for thigh bones of the male and female rats, and no clear difference was found.

Compound 1-3 was orally administered to the groups I to V and the dynamic indicators of the thigh bones observed, but it was necessary to repeat the test because of a failure in selection of the thigh bone material. The other groups were statistically analyzed with no clear differences found. This was due to the small number of animals. The test will have to be repeated.

Note: The flexural strength was referred to as the maximum breakage bending matrix and the value was calculated using the following formula.

$$\frac{1(25\ mm)}{4} XP = \frac{PL}{4}$$

(ix) Effect of the compound on osteosarcoma cell line UMR106 cells

1. Addition of $^3$H-TdR: $10^{-10}$M of $E_2$ had no effect on addition of $^3$H-TdR in UMR106 cells. $10^{-9}$M to $10^{-7}$M of $E_2$ clearly induced a peak value after addition of $^3$H-TdR to UMR106 cells, and the peak value changed to $10^{-7}$M, which was a 63% increase in comparison to the control group. Compared with the $E_2$ group, the stimulating effect of compound 1-3 at $10^{-10}$M and $10^{-8}$M on UMR106 cells mixed with $^3$H-TdR was clearly stronger at respectively, P<0.001 and P<0.05, and compound 1-3 at $10^{-9}$ M and $10^{-7}$M were 13% and 9% higher than $E_2$, respectively.

2. Measurement of number of cells: $E_2$ had no effect on the number of cells at $10^{-10}$M, but at $10^{-9}$M to $10^{-7}$M the cell count increased, and the peak was at $10^{-7}$M. Compound 1-3 clearly increased the number of cells at $10^{-10}$–$10^{-7}$M, with the peak concentration being $10^{-7}$ M. The effect of compound 1-3 was stronger than $E_2$, but there was no clear difference between the two.

3. Measurement of ALP activity: (1) Measurement of activity of ALP in amniotic fluid: $E_2$ had no effect on amnionic ALP activity at $10^{-10}$M. At $10^{-9}$–$10^{-7}$M, $E_2$ clearly increased ALP activity dose independently. Compound 1-3 also increased ALP activity in amniotic fluid at $10^{-10}$ to $10^{-7}$M in a dose-dependent manner. The effects were stronger than $E_2$ at all concentrations, with clear differences (P<0.001). (2) Measurement of activity of ALP secreted from culture solution: $E_2$ and compound 1-3 clearly stimulated an activity ALP secreted from UMR106 cells at all concentrations from $10^{-9}$ to $10^{-7}$M, and although $E_2$ had no effect on the enzyme at $10^{-10}$M, compound 1-3 at $10^{-10}$M and $10^{-7}$M produced enzyme activity which was 29% and 23% higher, respectively, than that of $E_2$ group. The compound 1-3 at $10^{-9}$ and $10^{-8}$M also had a stronger effect than the $E_2$ group.

Experiment 6: Experiment Report on Drug Effect of Compound 1-3 on Osteoporosis in Castrated Rats 1. Materials 1-1 Drugs.

All of the drugs used in this experiment were provided by a team under Prof. Zen Hu and were formulated according to request.

1-2 Animals.

Female SD rats, 3 months old, body weight 180–220 g, provided by West China University of Medical Science, Animal Laboratory Center.

2. Experiment method 2-1. Grouping of animals and administration

The animals were observed for 1 week prior to the experiment, of which 150 were selected and separated into 10 groups of 15 rats each.

Group 1 (Sham): Temporary operated group. Laparotomy was made and stomach of each animal was perfused with 1 ml of physiological saline 3 times a week.

Group 2 (OVX): Castrated group. Each animal was ovariectomized, and the stomach was perfused with 1 ml of physiological saline 3 times a week.

Group 3 (oral $E_2$): Orally administered $E_2$. Each animal was ovariectomized and the stomach was perfused 2 times a week, and only 0.8 mg/ml of 17β-estradiol was administered each time.

Group 4 (low oral): Orally administered compound 1-3 at low dosage. Each animal was ovariectomized and the stomach was perfused 3 times a week, and only 5 mg/ml was administered each time.

Group 5 (medium oral): Orally administered compound 1-3 at medium dosage. Each animal was ovariectomized and the stomach was perfused 2 times a week, and only 20 mg/ml was administered per rat each time.

Group 6 (high oral): Orally administered compound 1-3 at high dosage. Each animal was ovariectomized and the stomach was perfused 3 times a week, and only 80 mg/ml was administered each time.

Group 7 (injection $E_2$): Given $E_2$ injection. Each animal was ovariectomized and 200 µg/0.2 ml of 17-estradiol was injected 2 times a week, each time for the first 4 weeks and then at 7.5 µg/0.2 ml of 17β-estradiol was per rat for next 6 weeks.

Group 8 (low injection): Given low dose injection. Each animal was ovariectomized and 1 mg/0.2 mg of the compound 1-3 was injected 2 times a week, for the first 4 weeks and then 0.1 mg/0.2 ml was for the next 6 weeks.

Group 9 (medium injection): Given medium dose injection. Each animal was ovariectomized and 3.75 mg/0.2 ml of the compound 1-3 was injected 2 times a week, for the first 4 weeks and then 0.375 mg/0.2 ml for the next 6 weeks.

Group 10 (high injection): Given high dose injection. Each group was ovariectomized and 15 mg/0.2 ml of the compound 1-3 was injected 2 times a week, for the first 4 weeks and then 1.5 mg/0.2 ml for the next 6 weeks.

2-2 Butchering and observation of animals

At 11th week, animals were sacrificed by femoral arteriotomy and uterus was taken out. After that, measurement of BMD of right shank bone, pathohistological inspection of left shank bone, measurement of weight of right shank bone, biomechanics measurement of left thigh bone, measurement of ash of right thigh bone and biochemical finding and uterus weight were made.

2-3 Statistical analysis

All parameters were expressed by X±SD. The parameters of each group were compared with those of the castrated group, and the statistical level was 0.05.

3. Results 3-1. Effect of compound 1-3 on the body weight and the condition of whole body of castrated rats After 4 weeks from the start of the experiment, the rats in the group orally administered compound 1-3 at a high dose, the groups given low and medium dose injections thereof, and the group injected with $E_2$ exhibited erection of hair, inactive movement, epilation, etc., and therefore the administration was suspended for one week to all of the test animals. At the result of the administration of test compound with decreased dose for latter 6 weeks, the above-mentioned phenomena were diminished or disappeared. Upon completion of the experiments, all the groups exhibited a weight increase of about 30–40%, except for the group given a high oral dose of compound 1-3, in which the weight increase was suppressed (1.4%).

3-2. Biodynamic effect of compound 1-3 on bone of castrated rats

The bending resistance of the thigh bone of the Sham-operated rats was 97 newtons, and this decreased to 80 newtons in the castrated group. There was a clear difference between these two groups ($P<0.05$). The bending resistance of the thigh bone of the rats in the groups given $E_2$ orally and by injection rose to 101 and 90 newtons, respectively, which was a clear difference in comparison with the castrated group. The bending resistance of the thigh bones of the rats in the groups given low, medium and high oral doses of compound 1-3 were 105, 105 and 74 newtons, respectively, showing increases in the low and medium dose groups in comparison with the castrated group, with a clear difference. The bending resistance of the thigh bones of the rats in the groups given low, medium and high injection doses of compound 1-3 were 83, 103 and 97 newtons, respectively, with the medium and high dose groups showing clear differences in comparison with the castrated group. This experiment was completed with the cooperation of the West South Jiao Tong University Biomechanics Laboratory.

3-3. Effect of compound 1-3 on bone density of shank bone of castrated rats

The bone density of the castrated rat group was 0.037 g/cm and it was clearly lower than the temporary operated group (0.072 g/cm), and the bone density of the rats in the groups given $E_2$ orally and by injection increased to 0.057 and 0.065 g/cm, respectively. The bone densities of the rats in the groups given compound 1-3 orally at low, medium and high doses were 0.056, 0.062 and 0.064 g/cm, respectively. The bone densities of the rats in the groups given the compound by injection at low, medium and high doses were 0.054, 0.066 and 0.085 g/cm, respectively, and all of these were higher than the castrated group and the relationship was dose-dependent.

3-4. Effect of compound 1-3 on weight of ash of thigh bone of castrated rats

The average weight of the femoral ash of the rats in the Sham-operated group was 0.246 g/rat, and lower in the castrated group at 0.227 g/rat, which was a clear difference ($P<0.05$). The weight of ash of thigh bone of the groups given compound 1-3 orally and by injection were all clearly higher than the castrated group, and either same or higher the levels of the Sham-operated group.

3-5. Effect of compound 1-3 on thigh bone of castrated rats

The calcium content of the thigh bone of the castrated rats were clearly lower than that of the Sham-operated group or of any of the treated groups ($P<0.05$). The calcium content in thigh bone of the Sham-operated group was 308 mg/g, compared to 209 mg/g in the castrated group, 319 mg/g and 330 mg/g, respectively in the groups given $E_2$ orally and by injection, 315, 321 and 322 mg/g, respectively in the groups given compound 1-3 orally at low, medium and high doses, and 312, 315 and 322 mg/g, respectively in the groups given injection of compound 1-3 at low, medium and high doses. When compound 1-3 was administered orally or by injection, there was a constant dose-dependent relationship with the calcium contents in thigh bone in all cases.

3-6. Effect of compound 1-3 on physiological change of shank bone of castrated rats The bone-trabecula was normal in the pseudosurgery group. The bone-trabecula of the castrated group were somewhat sparse and narrow, and bone-trabecula like bone was increased. Wide sparse were found in some part of trabecular epiphyseal plate, and the bone-marrow cavity widened apparently. Absorption lacunae on the surface of trabecula and number of osteoclast increased apparently and become active. Osteoblast also increased but the action of osteoblast was much more active. The density and width of trabecula of the treated group with E2 and XW630 increased to some extent but button type trabecula decreased apparently and number of active osteoblast and osteoblast was decreasing.

3-7. Effect of compound 1-3 on uterine weight of castrated rats

The uterus of the castrated rats atrophied apparently and the weight also decreased (0.17 g), which was clearly lower than that of the sham-operated group (0.37 g). In the groups given $E_2$ orally and by injection, the weight of the uterus had clearly increased (0.40, 0.21). In the groups given compound 1-3 orally at low, medium and high doses, the uterus weight was 0.33, 0.45 and 0.48 g, respectively. In the groups given compound 1-3 by injection at low, medium and high doses, the uterine weights were 0.12, 0.23 and 0.40 g, respectively. The uterus weight in the groups given medium and high doses of compound 1-3 was clearly higher than that of the castrated group, unlike the groups given low doses orally and by injection.

3-8. See Table 10 for changes in indicators for compound 1-3 with comparison between each test group and the castrated group.

4. Intermediate Summary 4-1. When compound 1-3 was administered orally and by injection, there were notable effects on the bone trabecular contents, bone density, bone biomechanism and bone calcium contents of the castrated rats, and it was possible to effectively maintain the bone substance stability after castration. There were notable differences in comparison with the castrated group. Some of the numerical values reached to or exceeded the levels of the Sham-operated group. This experiment showed that the group given a high oral dose of compound 1-3 had an increase in bone mass as usual though exhibiting toxic symptoms, but the bending resistance of the bone was very low.

4-2. When compound 1-3 was administered orally or by injection, the effect on bone mass, bone density, bone biomechanism, bone ash weight and bone calcium content of the castrated rats was in a constant dose-dependent relationship.

4-3. The effect of compound 1-3 on the bone substance of the castrated rats under these experimental conditions either was same or exceeded the therapeutic effect of $E_2$.

4-4. When the compound was administered orally or by injection at a low dose, there were notable effects of improvement on all of the various parameters of bone substance of the castrated rats. When the compound was administered orally at a low dose, the uterus increased slightly, but did not reach the level of the sham-operated group. When compound 1-3 was injected at a low dose, there was no effect on the weight of the uterus of the rats. This demonstrated that effective doses of compound 1-3 with a prophylactic effect on bone loss in castrated rats either have slight stimulating activity to uterus or no action.

TABLE 10

Changes in indicators for compound 1-3 with comparison between each test group and OVX group

| Group | Indicator | | | | | | |
|---|---|---|---|---|---|---|---|
| | Bone density (2-photon) | Bone pathology (bone and muscle density, width) | Bone ash weight (g/rat) | Bone calcium (mg/g) | Bone flexural strength (newtons) | Uterine wet weight (g) | Improvement in physical condition (%) |
| Sham | — | — | — | — | — | — | — |
| OVX | ↓ | ↓ | ↓ | ↓ | ↓ | ↓ | ↓ |
| Oral $E_2$ | ↑ | ↑ | ↑ | ↑ | ↑ | ↑ | ↑ |
| Low oral | ↑ | ↑ | ↑ | ↑ | ↑ | ↑↓ | ↑ |
| Medium oral compound 1-3 | ↑ | ↑ | ↑ | ↑ | ↑ | ↑ | ↑ |
| High oral | ↑ | ↑ | ↑ | ↑ | ↑ | ↑ | ↑ |
| Injection $E_2$ | ↑ | ↑ | ↑ | ↑ | ↑ | ↑ | ↑ |
| Low injection | ↑ | ↑↓ | ↑ | ↑ | ↑ | ↑ | ↑ |
| Medium injection compound 1-3 | ↑ | ↑ | ↑ | ↑ | ↑ | ↑ | ↑ |
| High injection | ↑ | ↑ | ↑ | ↑ | ↑ | ↑ | ↑ |

Note: "—" = normal; "↓" = decrease or reduction; "↑" = increase, weight increase of >20%; "↑↓" = slight increase

We claim:

1. A pharmaceutical composition comprising a compound represented by the following formula (I):

x—Y—z   (I)

where X is a monovalent group represented by the following formula (II):

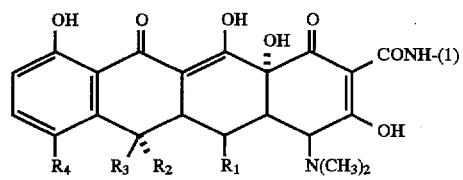

(where $R_1$ a is hydrogen or a hydroxyl group, $R_2$ is hydrogen or a hydroxyl group, $R_3$ is hydrogen or a methyl group and $R_4$ is hydrogen, halogen or a dimethylamino group);

Y is a divalent or trivalent group represented by the following formula (III), (IV) or (V):

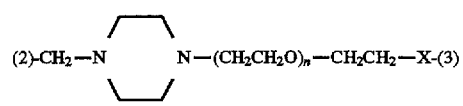

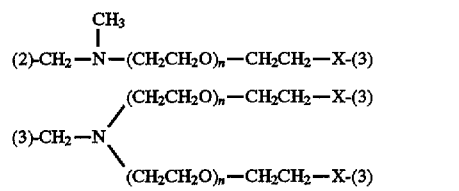

(where n is 0 to 4, and —X— is a direct bond, —O— or —NH—); and

Z is a monovalent group formed by removing a hydrogen atom or a hydroxyl group from a compound represented by the following formula (VI):

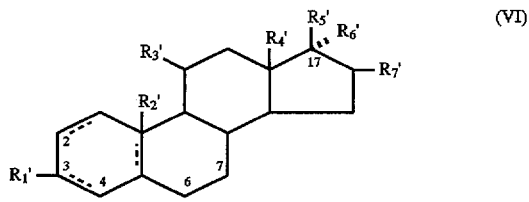

(where $R_1'$ is HO— or O=; $R_2'$ is a hydrogen atom or a methyl group; $R_3'$ is a hydrogen atom, a phenyl group or a substituted phenyl group; $R_4'$ is a methyl group or an ethyl group; $R_5'$ is a hydroxyl group, a ketone group or an acetyl group; $R_6'$ is hydrogen, a hydroxyl group, a methyl group, an ethynyl group or a propynyl group; or $R_5'$ and $R_6'$ together form =O; $R_7'$ is hydrogen, a hydroxyl group or =O, or $R_6'$ and $R_7'$ are together bonded to oxygen atoms of a 2,2-dioxypropyl group; and the symbol ... represents a single bond or a double bond); whereby this bond group exists at the 2-position, 3-position, 4-position, 6-position, 7-position or 17-position, or at the phenyl group bonded to the 11-position, (1) of the formula (II) and (2) of the formulas (III) to (V) are directly bonded, and (3) of the formulas (III) to (V) and any of the bond groups of the formula (VI) are directly bondeds.

2. A pharmaceutical composition according to claim 1, wherein said monovalent group represented by the formula (II) is a monovalent group of a tetracycline compound wherein $R_1$ is hydrogen, $R_2$ is hydroxyl group, $R_3$ is a methyl group and $R_4$ is hydrogen.

3. A pharmaceutical composition according to claim 1, wherein said monovalent group represented by the formula (II) is a monovalent group of Terramycin wherein $R_1$ is a hydroxyl group, $R_2$ is a hydroxyl group, $R_3$ is a methyl group and $R_4$ is methyl.

4. A pharmaceutical composition according to claim 1, wherein said monovalent group represented by the formula (II) is a monovalent group of chlorotetracycline wherein $R_1$ is hydrogen, $R_2$ is a hydroxyl group, $R_3$ is a methyl group and $R_4$ is chlorine.

5. A pharmaceutical composition according to claim 1, wherein said monovalent group represented by the formula (II) is a monovalent group of deoxytetracycline wherein $R_1$ is a hydroxyl group, $R_2$ is hydrogen, $R_3$ is a methyl group and $R_4$ is hydrogen.

6. A pharmaceutical composition according to claim 1, wherein said monovalent group represented by the formula (II) is a monovalent group of aminotetracycline wherein $R_1$ is hydrogen, $R_2$ is hydrogen, $R_3$ is hydrogen and $R_4$ is dimethylamino group.

7. A pharmaceutical composition according to claim 1, wherein said monovalent group represented by the formula (VI) is a monovalent group of estrogen wherein $R_5'$ and $R_6'$ together form =O and $R_7'$ is hydrogen.

8. A pharmaceutical composition according to claim 1, wherein said monovalent group represented by the formula (VI) is a monovalent group of estradiol wherein $R_5'$ is a hydroxyl group, $R_6'$ is hydrogen and $R_7'$ is hydrogen.

9. A pharmaceutical composition according to claim 1, wherein said monovalent group represented by the formula (VI) is a monovalent group of estroalkynol wherein $R_5'$ is a hydroxyl group, $R_6'$ is an ethynyl group and $R_7'$ is hydrogen.

10. A pharmaceutical composition according to claim 1, wherein said monovalent group represented by the formula (VI) is a monovalent group of estriol wherein $R_5'$ is a hydroxyl group, $R_6'$ is hydrogen and $R_7'$ is a hydroxyl group.

* * * * *